US012629396B2

(12) United States Patent
Xu et al.

(10) Patent No.: US 12,629,396 B2
(45) Date of Patent: May 19, 2026

(54) APPLICATION OF BACTERIA IN PREPARATION OF SYNERGIST FOR IMMUNE CHECKPOINT INHIBITOR

(71) Applicant: SUN YAT-SEN UNIVERSITY CANCER CENTER, Guangdong (CN)

(72) Inventors: Ruihua Xu, Guangdong (CN); Xia Zhao, Guangdong (CN)

(73) Assignee: SUN YAT-SEN UNIVERSITY CANCER CENTER, Guangdong (CN)

( * ) Notice: Subject to any disclaimer, the term of this patent is extended or adjusted under 35 U.S.C. 154(b) by 582 days.

(21) Appl. No.: 18/025,640

(22) PCT Filed: Jul. 12, 2022

(86) PCT No.: PCT/CN2022/105302
§ 371 (c)(1),
(2) Date: Mar. 9, 2023

(87) PCT Pub. No.: WO2023/284758
PCT Pub. Date: Jan. 19, 2023

(65) Prior Publication Data
US 2023/0346852 A1 Nov. 2, 2023

(30) Foreign Application Priority Data

Jul. 16, 2021 (CN) .......................... 202110808366.1
Aug. 16, 2021 (CN) .......................... 202110939699.8
Feb. 16, 2022 (CN) .......................... 202210143529.3

(51) Int. Cl.
| | |
|---|---|
| *A61K 35/741* | (2015.01) |
| *A61K 39/395* | (2006.01) |
| *A61K 41/10* | (2020.01) |
| *A61K 41/17* | (2020.01) |
| *A61P 35/00* | (2006.01) |
| *A61K 35/00* | (2006.01) |

(52) U.S. Cl.
CPC ........ *A61K 35/741* (2013.01); *A61K 39/3955* (2013.01); *A61K 41/10* (2020.01); *A61K 41/17* (2020.01); *A61P 35/00* (2018.01); *A61K 2035/115* (2013.01)

(58) Field of Classification Search
CPC ...................................................... A61K 35/741
USPC ........................................................ 424/133.1
See application file for complete search history.

(56) References Cited

U.S. PATENT DOCUMENTS

2019/0365829 A1 12/2019 Li et al.

FOREIGN PATENT DOCUMENTS

| | | |
|---|---|---|
| CN | 114159475 | 3/2022 |
| CN | 114668782 | 6/2022 |
| WO | 2020106983 | 5/2020 |

OTHER PUBLICATIONS

Erez N. Baruch et al., "Fecal microbiota transplant promotes response in immunotherapy-refractory melanoma patients" , Science, vol. 371, Issue 6529, Dec. 2020, pp. 1-16.
(Continued)

*Primary Examiner* — Sean E Aeder
(74) *Attorney, Agent, or Firm* — JCIPRNET

(57) ABSTRACT

The invention discloses an application of bacteria in preparation of a synergist for an immune checkpoint inhibitor. The bacteria are active bacteria or inactive whole-cell gut microbiota. By using a monobacterial oral preparation of human endogenous gut microbiota *Alistipes* combined with an immune checkpoint inhibitor, an anti-tumor immune protective response and an effect of remodeling gut microbiota is generated by stimulation of oral administration of active human commensal gut microbiota or inactive whole-cell human commensal gut microbiota, which significantly enhances an efficacy of the immune checkpoint inhibitor on multiple tumor species, enhances anti-tumor immune function, is conducive to improving the response rate of cancer immunotherapy populations, and has better safety, prolongs overall survival time of cancer patients, expands cancer patient population benefited from cancer immunotherapy (immunotherapy checkpoint inhibitors), provides new combination therapy regimens and therapeutic drugs to treat immune checkpoint inhibitor-refractory tumor patients, and expands the patient benefited from cancer immunotherapy.

14 Claims, 23 Drawing Sheets

Specification includes a Sequence Listing.

(56)                 References Cited

OTHER PUBLICATIONS

Lisa Derosa et al., "Microbiota-Centered Interventions: The Next Breakthrough in Immuno-Oncology?", Cancer Discovery, vol. 11, Issue 10, Oct. 2021, pp. 2396-2412.

Noriho Iida et al., "Commensal Bacteria Control Cancer Response to Therapy by Modulating the Tumor Microenvironment", Science, vol. 342, Nov. 2013, pp. 967-970.

Lukas F. Mager et al., "Microbiome-derived inosine modulates response to checkpoint inhibitor immunotherapy", Science, vol. 369, Issue 6510, Aug. 2020, pp. 1-17.

Bianca J. Parker et al., "The Genus Alistipes: Gut Bacteria With Emerging Implications to Inflammation, Cancer, and Mental Health", Frontiers in Immunology, vol. 11, Jun. 2020, pp. 1-15.

Bertrand Routy et al., "Gut microbiome influences efficacy of PD-1-based immunotherapy against epithelial tumors", Science, vol. 359, Issue 6371, Nov. 2009, pp. 1-13.

Ron Sender et al., "Essay Revised Estimates for the Number of Human and Bacteria Cells in the Body", PLOS Biology, vol. 14, Issue 8, Aug. 2016, pp. 1-14.

Michael Francisco et al., "Fecal microbiota potentiate checkpoint inhibitors, unleash microbiome startups", Nature Biotechnology, vol. 39, May 2021, pp. 529-532.

Ping Chen et al., "Progress in understanding the relationship between gut microbiota and immune checkpoint inhibitors", Chin J Clin Oncol, vol. 46, Issue 24, Dec. 2019, with English abstract, pp. 1292-1296.

"International Search Report (Form PCT/ISA/210) of PCT/CN2022/105302", mailed on Oct. 12, 2022, with English translation thereof, pp. 1-8.

A

B

C

SEQUENCE LISTING

```
Sequence total quantity: 1
SEQ ID NO: 1           moltype = DNA  length = 1487
FEATURE                Location/Qualifiers
source                 1..1487
                       mol_type = genomic DNA
                       organism = Alistipes finegoldii
SEQUENCE: 1
agagtttgat cctggctcag gatgaacgct agcggcaggc ttaacacatg caagtcgagg 60
ggcagcgggg agtagcaata ctccgccggc gaccggcgca cgggtgcgta acgcgtatgc 120
aacctacctt taacaggggc ataacactga gaaattggta ctaattcccc ataacattcg 180
agaaggcatc ttcttgggtt aaaaactccg gtggttaaag atgggcaggc gttgtattag 240
ctagttggtg aggtaacggc tcaccaaggc aacgatacat aggggactg agaggttaac 300
cccccacatt ggtactgaga cacggaccaa actcctacgg gaggcagcag tgaggaatat 360
tggtcaatgg acgcaagtct gaaccagcca tgccgcgtgc aggaagacgg ctctatgagt 420
tgtaaactgc ttttgtacta gggtaaacgc ttttacgtgt aggagcctga aagtatagta 480
cgaataagga tcggctaact ccgtgccagc agccgcggta atacggagga tccaagcgtt 540
atccggattt attgggttta aagggtgcgt aggcggtttg ataagttaga ggtgaaatac 600
cggggctcaa ctccggaact gcctctaata ctgttgaact agagagtagt tgcggtaggc 660
ggaatgtatg gtgtagcggt gaaatgctta gagatcatac agaacaccga ttgcgaaggc 720
agcttaccaa actatatctg acgttgaggc acgaaagcgt ggggagcaaa caggattaga 780
taccctggta gtccacgcag taaacgatga taactcgttg tcggcgatac acagtcggtg 840
actaagcgaa agcgataagt tatccacctg gggagtacgt tcgcaagaat gaaactcaaa 900
ggaattgacg ggggcccgca caagcggagg aacatgtggt ttaattcgat gatacgcgag 960
gaaccttacc cgggcttgaa agttagtgac gattctggaa acaggatttc ccttcggggc 1020
acgaaactag gtgctgcatg gttgtcgtca gctcgtgccg tgaggtgtcg ggttaagtcc 1080
cataacgagc gcaacccta ccgttagttg ccatcaggtc aagctgggca ctctggcggg 1140
actgccggtg taagccgaga ggaaggtggg gatgacgtca aatcagcacg gcccttacgt 1200
ccggggctac acacgtgtta caatggtagg tacagagggc cgctaccccg cgagggatg 1260
ccaatctcga aagcctatct cagttcggat cggaggctga aacccgcctc cgtgaagttg 1320
gattcgctag taatcgcgca tcagccatgg cgcggtgaat acgttcccgg gccttgtaca 1380
```

-continued

```
caccgcccgt caagccatgg aagctggggg tgcctgaagt tcgtgaccgc aaggagcgac  1440
ctagggcaaa accggtgact ggggctaagt cgtaacaagg taaccaa                1487
```

APPLICATION OF BACTERIA IN PREPARATION OF SYNERGIST FOR IMMUNE CHECKPOINT INHIBITOR

CROSS-REFERENCE TO RELATED APPLICATION

This application is a 371 of international application of PCT application serial no. PCT/CN2022/105302, filed on Jul. 12, 2022, which claims the priority benefit of China application no. 202110808366.1, filed on Jul. 16, 2021, China application no. 202110939699.8, filed on Aug. 16, 2021, and China application no. 202210143529.3, filed on Feb. 16, 2022. The entirety of each of the above-mentioned patent applications is hereby incorporated by reference herein and made a part of this specification.

TECHNICAL FIELD

The invention relates to the technical field of tumor treatment, and specifically relates to an application of bacteria in treating tumor.

BACKGROUND

Malignant tumors are currently one of the biggest problems facing the world. Among the various lethal factors that cause death each year, malignant tumors rank first. A conventional therapy, such as a surgery, radiotherapy and chemotherapy, is difficult to completely eliminate cancer cells, and thus there is a high recurrence rate, and the treatment methods such as radiotherapy and chemotherapy are not highly targeted, which can kill cancer cells and are lethal to normal cells at the same time, causing great harm to patients and seriously affecting life quality of patients.

Compared with the conventional therapy, a target of tumor immunotherapy is not tumor cells and tissues, but the human body's own immune system. By regulating and activating the human immune system, it relies on autoimmune mechanism to eliminate tumor cells, including tumor cells that have metastasized to distant places, which has little side effect on normal cells, and greatly improves prognosis and life quality of patients with advanced malignant tumors. Immunopotentiators are a new class of drugs, also known as immunomodulators, formerly known as immunizing boosters and immunostimulants. Most of the immunopotentiators are developed for purpose of non-specific immunotherapy of tumors, which play a therapeutic role by improving the body's immune function and accelerating induction of immune response. Clinically, they are mainly used for adjuvant therapy of immunodeficiency diseases, malignant tumors, and refractory bacterial or viral infections. The commonly used immunopotentiator drugs in clinic are divided into five categories according to their sources:

1. Bacterial-derived immunopotentiator drugs, such as BCG;
2. Human or animal immune system products, such as thymosin, transfer factor, interferon, interleukin, etc.;
3. Chemically synthesized immunopotentiator drugs, such as levamisole, polyinosinic acid, etc.;
4. Fungal polysaccharides, such as lentinan, etc.;
5. Traditional Chinese medicine and others, such as ginseng, astragalus and other active ingredients of traditional Chinese medicine; phytohemagglutinin (PHA), concanavalin A and placental polysaccharide, etc.

The application of bacterial-derived immunopotentiators in cancer treatment has a long history. As early as 1893, William Coley, a pioneer in the field of cancer immunity, used "Coley toxin" prepared from Streptococcus pyogenes to repeatedly inoculate advanced cancer patients, stimulating fever and the body to produce immune responses, which could lead to tumor regression in some patients. "Coley toxin" has become a cornerstone of cancer immunotherapy, prompting a rise of modern cancer immunotherapy. The unprecedented rise and success of cancer immunotherapy over the past decade has revolutionized the clinical management of multiple malignant tumors. Among them, Immune-Checkpoint Inhibitors (ICIs) are one of the most cutting-edge technologies in immunotherapy.

There are currently many cancer immunotherapies, among them immune checkpoint inhibitors (ICIs) therapy is to reactivate T cells and reactivate the immune system to recognize and remove tumor cells by blocking immunosuppressive pathways (such as PD-1/PD-L1 and CTLA-4/B7-1) hijacked by tumor cells, which has advantages of good efficacy and long-lasting response, creating a new era of cancer treatment. The application of ICIs is a milestone in the field of immuno-oncology, especially in the subset of patients with unresectable diseases, has revolutionized anticancer treatment.

At present, ICIs provides long-term clinical benefits to patients, even after treatment interruption, which increases hope of cure for some patients. Especially in melanoma patients, who can achieve a complete remission, that is, all visible tumor metastases disappear completely. Nevertheless, the low response rate ICIs therapy remains to be resolved. Only 15% to 40% of patients can achieve the complete remission in the single-agent ICIs treatment. There is an urgent need to develop a combination strategy to synergize efficacy of ICIs.

The current mainstream combination strategies include ICIs plus surgery, chemotherapy, radiotherapy, targeted therapy and other treatment methods, which can produce a synergistic effect, enhance the durability and efficacy of ICIs, and increase overall response rate of ICIs. Although these combination therapies can improve the efficacy and the response rate of ICIs to a certain extent, toxicity is usually increased accordingly.

Studies have found that factors related to patient response heterogeneity or resistance to ICIs treatment include not only tumor internal factors, such as tumor microenvironment, but also host-related factors, such as age, genetic diversity, diet, gut microbiota and other factors. It is the most interesting that some specific gut microbiota have an effect on efficacy of ICIs through colonization or a direct interaction of their own whole-cell components with intestinal mucosal immune system or an indirect interaction of small molecule metabolites generated through their metabolic functions. Therefore, among these combination therapies, multiple studies on assisting the implications for modulating the gut microbiome in ICIs treatment have become milestones in the field of tumor treatment. Intestine is the largest lymphoid organ in our body by virtue of lymphocyte numbers and quantity of immunoglobulin produced, with more than 70% T cells, and is the residence of most memory T cells. Through interaction with intestinal immune organs, gut microbiome promotes a development of immune system, balances and establishes an immune tone. For the human body's defense system and immune system, bacteria and tumors are "non-self". Therefore, the human body uses the same set of defense mechanisms in its immune response to bacteria and tumors, and the immune response stimulated by gut microbiome also has anti-tumor potential. Based on this anti-tumor immunology cross theory of the gut microbiome and an oncolytic enzyme secreted by certain bacteria, bacteria have been used for tumor treatment for hundreds of years. It is worth noting that the anti-tumor effect induced by the gut microbiota is derived from the body's own immune response. Thus, compared with the combination therapies of radiotherapy or chemotherapy, it has higher safety and fewer side effects.

A review published on Cancer Discovery, August 2021 summarizes 38 studies published from 2017 to 2020, where an analysis involved 11,959 cancer patients treated with ICIs shows use of antibiotics before or during immunotherapy significantly reduced survival rate of patients (Hazard Ratio HR=1.81, p=0.03), indicating that immune responses induced by gut microbiota has an important role in promoting the efficacy of ICIs therapy (Derosa, Routy et al. 2021). A number of clinical studies at home and abroad have shown that pathways for manipulating gut microbiota, such as fecal microbiota transplant, oral administration of pure strains and prebiotics, combined with ICIs therapy, can reverse the resistance of tumor patients to ICIs, which indicates that local therapy based on intervention of gut microbiota can support gut immunity, stimulate effective antitumor immune surveillance, and trigger durable distal antitumor immunity. Two recent clinical trials reported that accepting fecal microbiota transplant from ICIs treatment responders (achieving a partial or complete remission) enables ICIs-refractory melanoma patients to achieve a partial or complete remission without toxic side effects, which strongly proves the synergistic effect of commensal gut microbiome on ICIs therapy (Baruch EN 2020, Zipkin 2021). However, fecal microbiota transplant contains complex components. Complete fecal microbiome may play a role in fecal microbiota transplant, and the gut microbiota are greatly affected by environment, diet, and lifestyle. An inability to obtain a stable source of donor fecal microbiota limits a clinical application of fecal microbiota transplant combination immunotherapy with ICIs. Therefore, identification and preparation of a single-component anti-tumor symbiotic microbe with standardized quantitative production has become the key to solve this problem. In a recent study, researchers isolated three bacterial species from a ICIs treated mouse model: *Bifidobacterium pseudolongum*, *Lactobacillus johnsonii* and *Olsenella* species. These three bacterial species significantly enhanced efficacy of ICIs in four mouse models of cancer. Further investigation showed that *Bifidobacterium pseudolongum* can exert a synergistic effect of ICIs through production of the metabolite inosine (Mager LF 2020).

The convergence of fields from biology and chemistry to materials science, engineering, and computer science has opened up new avenues for the development of novel gut microbiota-derived immunopotentiators. The powerful combination of gut microbiota-derived immunopotentiators and immune checkpoint inhibitors will become a breakthrough in a new generation of tumor immunotherapy, providing alternative treatment options for immunotherapy-refractory tumor patients.

*Alistipes* belongs to a genus of *Bacteroidetes*, Gram-negative, obligate anaerobic, and are intestinal symbiotic bacteria. Based on hints of existing researches, *Alistipes* is a relatively new bacterial genus isolated from clinical samples. *Alistipes* contains diverse and complex species composition. Different *Alistipes* species have unique functional properties, which play a role in health-promoting or pathogenic effect on the human body (Parker, Wearsch et al.

2020). According to the NCBI taxonomy database, the currently identified and named *Alistipes* consist of 15 species, including *Alistipes communis, Alistipes dispar, Alistipes finegoldii, Alistipes ihumii, Alistipes indistinctus, Alistipes inops, Alistipes massiliensis, Alistipes megaguti, Alistipes okayasuensis, Alistipes onderdonkii, Alistipes provencensis, Alistipes putredinis, Alistipes senegalensis, Alistipes shahii, Alistipes timonensis*. Besides, included are about 90 *Alistipes* species not named or predicted from metagenomic sequencing data. According to the database of typical strains (Type Strain Genome), there are 14 culturable typical strains of *Alistipes* species with accession numbers. At present, there are only two *Alistipes* species suggested to have potentiated immunotherapy function in animal experiments: *Alistipes shahii* and *Alistipes indistinctus* (Iida N 2013, Routy B 2018). Whether other *Alistipes* species, or combinations of *Alistipes* species, can act as potentiators of gut microbiota-derived immune checkpoint inhibitors remains to be explored.

From an ecological niche of view, various species of *Alistipes* mainly exist in the gut of healthy people and play an important role in healthy maintenance of human intestinal immune status. For example, the reduction of *Alistipes* promotes the reduction of short-chain fatty acids, which may exacerbate advanced fibrosis in patients with non-alcoholic fatty liver disease. However, individual *Alistipes* species were also isolated from other human fluids, for example, *Alistipes onderdonkii* and *Alistipes shahii* was isolated from human abdominal abscess and appendix tissue as well as urine, respectively, reflecting the potential opportunistic pathogenicity of individual *Alistipes* species.

In an implementation case based on the previous patent application CN 110582291A, it is compared that effects of different single bacteria and bacterial species combinations such as alone *Akkermansia municiphila, Enterococcus hirae*13144, *Alistipes indistinctus* and a combination of *Akkermansia municiphila+Enterococcus hirae* 13144 as compensatory anticancer probiotics on reversal of immune checkpoint inhibitor-resistant tumor responses in the mouse MCA205 mouse fibrosarcoma model. The results showed that the selected single bacteria or bacterial species combination can significantly reduce final tumor size in mice with spontaneous gut microbiota reconstitution after antibiotic treatment without FMT or with FMT (derived from feces of two patients with no response to immune checkpoint inhibitors treatment), where the best responder group was oral gavage of *Akkermansia municiphila+Enterococcus hirae* 13144. One of the best surrogate markers for activity of an effective anticancer probiotic combination is upregulation of PD-L1 expression on circulating blood (or spleen) CD4+ or CD8+ T cells or upregulation of CCR9 on circulating T cells. Compared with the single-agent PD1 group, combination of PD1 with *Akkermansia municiphila+Enterococcus hirae* 13144 can significantly increase spleen tissue CD8+PDL1+ and CD4+PDL1+ immune cells, while the group of combination of PD1 with *Alistipes indistinctus* did not show significantly increased spleen tissue CD8+PDL1+ and CD4+PDL1+ immune cells. Different compensatory anticancer probiotic combinations are also compared in CN 110582291A, including two *Alistipes* species (*Alistipes oderdonkii+Alistipes finegoldii*). The results showed it was not the combination of more had better therapeutic effect, a combination of *Akkermansia municiphila+Enterococcus limosum* has the best response, while a combination of

*Alistipes oderdonkii+Alistipes finegoldii* did not show an effect of increasing efficacy of single-agent PD1 antibody.

SUMMARY OF THE INVENTION

*Alistipes finegoldii* that the present invention relates to is abbreviated as Af in its priority-based prior applications CN202110808366.1 and CN202110939699.8, abbreviated as RX-af01 in its priority-based prior application CN202210143529.3, and thus abbreviated as Af in this application.

An objective of the present invention is to provide an application of symbiotic bacteria in preparation of synergists for immune checkpoint inhibitors.

The present invention relates to a combination therapy that enhances efficacy of immune checkpoint inhibitors, suitable for one or more tumors.

A synergist for potentiating efficacy of the immune checkpoint inhibitors according to the present invention is a bacterium, preferably *Alistipes finegoldii* (Af), and the Af is selected from one or more of active bacteria, inactive whole-cell bacteria, bacterial derivatives or bacterial metabolites of *Alistipes finegoldii.*

The cancer immunotherapy of the present invention is selected from an immune checkpoint inhibitors therapy, the potentiating cancer immunotherapy is manifested as prolonging overall survival time of cancer patients, increasing a response rate of cancer immunotherapy population, or expanding cancer patient population benefited from cancer immunotherapy.

In the disclosed experimental data of the present invention, comparing gut microbiota after treatment of responder or non-responder cancer patients of immune checkpoint inhibitory anti-PD1 antibody (αPD-1) combined with chemotherapy, the response of responder patients to *Alistipes* significantly higher than that of non-responder patients, whereas this difference was not present in the chemotherapy-alone population. In the gut of colorectal cancer patients (CRC) who received αPD-1 in combination with chemotherapy, the progression-free survival (PFS) of *Alistipes*-positive patients was significantly longer than that of *Alistipes*-negative patients. In the gut of esophageal cancer (ESCC) patients treated with αPD-1 combined with chemotherapy, the survival (OS) of patients with high relative abundance of *Alistipes* was significantly longer than that of patients with low relative abundance of *Alistipes*. Among the five *Alistipes* species detected, the relative abundance of *Alistipes finegoldii* in the gut of ESCC and CRC patients with PFS greater than 6 months was significantly higher than that of patients with PFS less than 6 months after receiving αPD-1 combined with chemotherapy.

In various tumor models, the inventors found that administration of *Alistipes shahii* alone or administration of a combination of *Alistipes shahii+Alistipes finegoldii* could not achieve the effect of potentiating immune checkpoint inhibitors. While administration of active *Alistipes finegoldii* alone or inactive whole-cell *Alistipes finegoldii* combined with immune checkpoint inhibitors shows that *Alistipes finegoldii* or its inactive bacterial components can be used as synergists of immune checkpoint inhibitors in cancer treatment, enhancing the body's tumor-killing immune function.

A treatment method provided by the present invention has significant improvements on shortcomings of conventional therapies: large side effects, easy metastasis and recurrence, short duration, short survival, and poor life quality; and it has significant improvements on shortcomings of single-agent immune checkpoint inhibitors therapy: a limited range of tumor types affected and small population with drug responses; and it has significant improvements on shortcomings of immune checkpoint inhibitors combined with radiotherapy or chemotherapy: large side effects, small population with drug responses.

The treatment method provided by the present invention has a good therapeutic effect when treating the following patients: treating tumor patients who cannot have a surgery, and for whom no targeted drug is available and radiotherapy and chemotherapy are ineffective; treating tumor patients for whom single-agent immune checkpoint inhibitor is ineffective or who has drug resistance (primary, adaptive and accessible resistance); treating tumor patients for whom immune checkpoint inhibitor combination therapies with radiotherapy, hemotherapy and target therapy are ineffective or who has drug resistance (primary, adaptive and accessible resistance).

The present invention achieves the above-mentioned invention objectives through the following solutions.

It is provided an application of bacteria in tumor treatment.

Preferably, the bacterium is one or more of active bacteria, inactive bacteria, bacterial derivatives, and bacterial metabolites.

Preferably, the inactive bacteria are inactive whole-cell bacteria.

Preferably, the active bacteria are intact bacteria and/or intact viable bacteria.

Preferably, the application is an application of bacteria as an active ingredient in preparation of a synergist for immune checkpoint inhibitors.

Preferably, the application is an application as a synergist for immune checkpoint inhibitors to improve the effect of immune checkpoint inhibitors in tumor treatment.

Preferably, the bacterium belongs to the genus *Alistipes*, that is, a 16S rDNA sequence of a strain of the bacterium has at least 85%, at least 90%, at least 95%, at least 96%, at least 97%, at least 98%, at least 99%, at least 99.5% or 100% consistency with a 16S rDNA sequence of *Alistipes*.

Preferably, the bacterium belonging to the genus *Alistipes* is one of or a combination of more of species or strains of bacteria belonging to the genus *Alistipes*.

More preferably, the bacterium belonging to the genus *Alistipes* is *Alistipes finegoldii.*

Further preferably, a 16S rDNA sequence contained in the *Alistipes finegoldii* has at least 99% consistency with a 16S rDNA sequence of *Alistipes finegoldii* species.

Further preferably, a 16S rDNA sequence contained in the *Alistipes finegoldii* has at least 99.5% or 100% consistency with a 16S rDNA sequence of a strain of *Alistipes finegoldii* DSM17242.

Even further preferably, the *Alistipes finegoldii* is one of or a combination of more of strains of *Alistipes finegoldii.*

Still even further preferably, the strain of *Alistipes finegoldii* is one of or a combination of more of *Alistipes finegoldii* DSM 17242, *Alistipes finegoldii* D53t1_180928_D3, *Alistipes finegoldii* 2789STDY5834947, *Alistipes finegoldii* 1001713B170207_170306_H2, *Alistipes finegoldii* DFI.2.31, *Alistipes finegoldii* BIOML-A1, *Alistipes finegoldii* DFI.2.16, *Alistipes finegoldii* DFI.2.10, *Alistipes finegoldii* aa_0143, *Alistipes finegoldii* 2789STDY5608890, *Alistipes finegoldii* MGBC116453, *Alistipes finegoldii* COPD076, or *Alistipes finegoldii* UBG195, with strain name of sub species classification in a genome database of NCBI (National Center for Biotechnology Information) (https://www.ncbi.nlm.nih.gov/genome/browse/#!/prokaryotes/11196/).

Even further preferably, the administration of *Alistipes finegoldii* is one of or a combination of more of following strains:

*Alistipes finegoldii* strain deposited at German collection of microorganisms and cell cultures DSMZ (Deutsche Sammlung von Mikroorganismen and Zellkulturen=German collection of microorganisms and cell cultures), under accession number DSM17242 (NCBI: txid679935, https://www.ncbi.nlm.nih.gov/Taxonomy/Browser/wwwtax.cgi?id=679935);

*Alistipes finegoldii* strain deposited at Japan JCM Culture Collection (Japan Collection of Microorganisms), under accession number JCM 16770;

*Alistipes finegoldii* strain deposited at Korean KCTC Culture Collection (Korean Collection for Type Cultures), with under accession number KCTC 15236;

*Alistipes finegoldii* strain deposited at Finland Helsinki Anaerobe Reference Laboratory (Anaerobe Reference Laboratory, Helsinki Collection, National Public health Institute, Helsinki, Finland), under accession number AHN 2437;

*Alistipes finegoldii* strain deposited at Sweden CCUG Culture Collection (Culture Collection University of Gothenburg), under accession number CCUG 46020;

*Alistipes finegoldii* strain deposited at French CIP Culture Collection (Collection de L'Institut Pasteur of Institut Pasteur), under accession number CIP 107999; and

*Alistipes finegoldii* strain deposited at Guangdong Microorganism Culture Collection, under accession number GDMCC 1.2324.

Preferably, a 16S rDNA sequence contained in the *Alistipes finegoldii* has at least 99% consistency with a 16S rDNA sequence of *Alistipes finegoldii* species, the 16S rDNA sequence of the *Alistipes finegoldii* is shown in SEQ ID NO: 1.

More preferably, the *Alistipes finegoldii* used in the invention is the strain deposited at DSM under accession number 17242.

More preferably, the bacterium belonging to the genus *Alistipes* and an immune checkpoint inhibitor are administered simultaneously or separately.

Preferably, the bacterial metabolites include all molecules produced or modified by the bacterium as a result of bacterial growth, survival, retention, transport or existence during bacteria preparation and storage and during mammalian gastrointestinal transport.

More preferably, the bacterial metabolites include all organic acids, inorganic acids, alkalis, proteins and peptides, enzymes and coenzymes, amino acids and nucleic acids, carbohydrates, lipids, glycoproteins, lipoproteins, glycolipids, vitamins, all bioactive compounds, metabolites containing inorganic components and all small molecules, such as nitrogen-containing molecules or sulfite-containing molecules.

Preferably, the bacterial derivatives include a bacterial constituent and a genetic material and related components, examples of which include bacterial cell membrane, pili, flagella, LPS, nucleic acid material and and other components derived from the bacterium.

Preferably, the inactive whole-cell bacteria are obtained by first culturing and expanding the bacteria and then inactivating them by various means.

More preferably, inactivation method of the bacteria is selected from any one or more of high temperature and/or high pressure inactivation, ultraviolet inactivation, radiation inactivation or inactivation of chemical agents such as formaldehyde, acetone, and phenol.

Further preferably, the chemical agent is any one or more of formaldehyde, acetone, and phenol.

More preferably, the inactive whole-cell bacteria include one or more of bacterial whole-cell components, bacterial whole-cell derivatives, or bacterial whole-cell metabolites.

More preferably, the bacterial whole-cell components include one or more of bacterial components and genetic material and related components, specifically, including bacterial cell walls, cell membranes, pilli, flagella, LPS, nucleic acid substances and other components derived from bacteria.

More preferably, the bacterial whole-cell derivatives include one or more of bacterial extracellular vesicles, bacterial-associated exosomes, and prophages.

More preferably, the bacterial whole-cell metabolites refer to the metabolites produced by the participation of bacterial whole-cell components, including all organic acids, inorganic acids, bases, proteins and peptides, enzymes and coenzymes, amino acids and nucleic acids, carbohydrates, lipids, glycoproteins, lipoproteins, glycolipids, vitamins, all biologically active compounds, metabolites containing inorganic components, and one or more of all small molecules, such as nitrogen-containing molecules or sulfite-containing molecules.

Preferably, the tumor treatment is manifested as shrinking or stabilizing a tumor, prolonging total survival time, prolonging a progression-free survival, and improving a life quality.

Preferably, the tumor is a adenomas, a malignant tumor, and a adenocarcinoma, wherein the tumor is classified according to a tissue origin or a cell name, including one or more of adrenocortical carcinoma, bladder urothelial carcinoma, breast cancer, pancreatic cancer, cervical cancer, cholangiocarcinoma, colon cancer, colorectal cancer, diffuse large B-cell lymphoma, glioblastoma multiforme, glioma, head and neck cancer, chromophobe renal cell carcinoma, mixed renal cancer, kidney cancer, leukemia, lymphadenoma, brain cancer, liver cancer, lung adenocarcinoma, lung squamous cell carcinoma, mesothelioma, ovarian cancer, pancreatic cancer, pheochromocytoma, paraganglioma, prostate cancer, rectal adenocarcinoma, sarcoma, skin melanoma, stomach cancer, esophageal cancer, testicular cancer, thyroid cancer, thymic cancer, endometrial cancer, uterine sarcoma, uveal melanoma, and soft tissue sarcoma.

In a specific embodiment of the present invention, the bacterium (Af) is an active bacterium of *Alistipes finegoldii* strain deposited at DSM under accession number 17242, and the tumor is colorectal cancer or melanoma, the immune checkpoint inhibitor is PD-1 monoclonal antibody (αPD-1), with a clone number G4C2, or CTLA4 monoclonal antibody (αCTLA4), with clone number 9D9.

In a specific embodiment of the present invention, the bacterium (Af) is an inactive bacterium of *Alistipes finegoldii* strain deposited at DSM under accession number 17242, and the tumor is colon cancer or lung cancer, the immune checkpoint inhibitor is αPD-1, with clone number G4C2.

Preferably, the tumor is a malignant tumor, a metastatic tumor or a non-metastatic tumor.

Preferably, the tumor described herein includes malignant, metastatic and non-metastatic types; including any stage of cancer (clinical stage I, II, III or IV, malignant tumor TNM classification T1-4, N0-4, or M0-1, and histological grade G1, G2, G3 or G4, etc.)

More preferably, the immune checkpoint inhibitor is one of or a combination of more of blockers acting on T cell negative costimulatory (coinhibitory) molecules and/or their respective ligands.

Further preferably, the T cell negative costimulatory (coinhibitory) molecules and/or their respective ligands are selected from one of or a combination of any of CTLA-4, PD-1, PD-L1, PD-L2, B7-1, B7-2, B7-H3, B7-H4, B7-H6, A2AR, IDO, TIM-3, BTLA, VISTA, TIGIT, LAG-3, CD40, KIR, CEACAM1, GARP, PS, CSF1R, CD94/NKG2A, TDO, TNFR, and DcR3.

Still further preferably, the blockers acting on the T cell negative costimulatory (coinhibitory) molecules and/or their respective ligands is selected from one of or a combination of any of nivolumab (PD-1 monoclonal antibody), ipilimumab (CTLA-4 monoclonal antibody), pembrolizumab (PD-1 monoclonal antibody), azetolizumab (PD-L1 monoclonal antibody), atezolizumab (PD-L1 monoclonal antibody), camrelizumab (PD-L1 monoclonal antibody), tislelizumab (BGB-A317), durvalumab (PD-L1 monoclonal antibody), tremelimumab (CTLA-4 monoclonal antibody), spartalizumab (PD-1 monoclonal antibody), avelumab (PD-L1 monoclonal antibody), sintilimab (PD-1 monoclonal antibody), toripalimab (PD-1 monoclonal antibody), cemiplimab (PD-1 monoclonal antibody), MGA012 (retifanlimab, PD-1 monoclonal antibody), MGD013 (tebotelimab, PD-1/LAG-3 double antibody), MGD019 (PD-1/CTLA-4 double antibody), enoblituzumab (B7-H3 monoclonal antibody), MGD009 (B7-H3 monoclonal antibody)), MGC018 (B7-H3 monoclonal antibody), MEDI0680 (PD-1 monoclonal antibody), PDR001 (PD-1 monoclonal antibody) FAZ053 (PD-L1 monoclonal antibody), PDR001FAZ053, TSR022 (TIM-3 monoclonal antibody), MBG453 (TIM-3 monoclonal antibody), relatlimab (BMS986016, LAG-3 monoclonal antibody), LAG525 (LAG-3 monoclonal antibody), IMP321 (LAG-3 monoclonal antibody), REGN3767 (LAG-3 monoclonal antibody), pexidartinib, CSF-1R monoclonal antibody), LY3022855 (CSF-1R monoclonal antibody), FPA008 (CSF-1R monoclonal antibody), BLZ945 (CSF-1R monoclonal antibody), GDC0919 (navoximod, IDO monoclonal antibody), epacadostat (IDO monoclonal antibody), indoximid (IDO monoclonal antibody), BMS986205 (IDO monoclonal antibody), CPI-444 (A2AR monoclonal antibody), MEDI9447 (oleclumab, CD73 monoclonal antibody), PBF509 (A2AR monoclonal antibody), and lirilumab (KIR monoclonal antibody); preferably the blocker is selected from one of or a combination of any of nivolumab, pembrolizumab, toripalimab, sintilimab, and cemiplimab.

Still further preferably, the immune checkpoint inhibitors are inhibitors that acts on PD-1/PD-L1 signaling pathway and/or PD-1/PD-L2 signaling pathway, wherein PD-1 refers to programmed cell death protein 1, and PD-L1 (B7-H1 or CD274) and PD-L2 (B7-DC or CD273) are ligands of PD-1.

Even still further preferably, the inhibitor of the PD-1/PD-L1 signaling pathway and/or the PD-1/PD-L2 signaling pathway is selected from one of or a combination of any of nivolumab (PD-1 monoclonal antibody), pembrolizumab (PD-1 monoclonal antibody), azetolizumab (PD-L1 monoclonal antibody), atezolizumab (PD-L1 monoclonal antibody), camrelizumab (PD-L1 monoclonal antibody), tislelizumab (BGB-A317), durvalumab (PD-L1 monoclonal antibody), spartalizumab (PD-1 monoclonal antibody), avelumab (PD-L1 monoclonal antibody), sintilimab (PD-1 monoclonal antibody), toripalimab (PD-1 monoclonal antibody), cemiplimab (PD-1 monoclonal antibody), MGA012 (retifanlimab, PD-1 monoclonal antibody), MGD013 (tebotelimab, PD-1/LAG-3 double antibody), MGD019 (PD-1/CTLA-4 double antibody), MEDI0680 (PD-1 monoclonal antibody), PDR001 (PD-1 monoclonal antibody), and FAZ053 (PD-L1 monoclonal antibody).

Still further preferably, the inhibitor of the PD-1/PD-L1 signaling pathway or the PD-1/PD-L2 signaling pathway is selected from one of or a combination of any of ipilimumab, tremelimumab, and MGD019.

Still further preferably, the immune checkpoint inhibitor is an inhibitor that acts on CTLA-4/B7-1 signaling pathway and/or CTLA-4/B7-2 signaling pathway, wherein CTLA-4 refers to cytotoxic T lymphocyte protein 4, and B7-1 (CD80) and B7-2 (CD86) are ligands of CTLA-4.

Even still further preferably, it can be selected from ipilimumab (CTLA-4 monoclonal antibody), tremelimumab (CTLA-4 monoclonal antibody), MGD019 (PD-1 and CTLA-4 double antibody) or any combination thereof.

As a specific embodiment of the present invention, the immune checkpoint inhibitor is an inhibitor that acts on PD-1/PD-L1 signaling pathway and/or PD-1/PD-L2 signaling pathway and/or an inhibitor that acts on CTLA-4/B7-1 signaling pathway and/or CTLA-4/B7-2 signaling pathway.

Specifically, the immune checkpoint inhibitor is a PD-1 monoclonal antibody or a CTLA-4 monoclonal antibody.

Preferably, chemotherapy, immunotherapy or radiotherapy is performed simultaneously, separately or sequentially with the administration of Af.

Preferably, an administration subject of the application is a human being, and the human being is an infant, a child, a teenager, an adult, or an elderly person.

Preferably, the administration subject of the application is a non-human primate, and the non-human primate is a mammal (such as a dog, a cat, a ferret, a horse, a rabbit, a guinea pig, a gerbil, a hamster, a squirrel, a rat, and a mouth); a bird; a reptile; fish; an amphibian; an arthropod or a livestock animal (such as a cattle, a pig, a sheep, a goat, an alpaca, a donkey, a camel, a buffalo or a mink).

Preferably, the bacterium (Af) is administered with a dose containing bacteria between $10^5$ and $10^{12}$ CFU (colony forming units), or between $10^7$ and $10^{11}$ CFU, or between $10^8$ and $10^{11}$ CFU, or between $10^9$ and $10^{11}$ CFU, or between $10^{10}$ and $10^{11}$ CFU, and more preferably, it is administered with a dose containing bacteria between $10^9$ and $10^{11}$ CFU.

The present invention further provides the following contents.

A kit for tumor treatment is provided, which contains one or more of immune checkpoint inhibitors, and the bacterium;

or consists of one or more of immune checkpoint inhibitors, and the bacterium.

Preferably, the kit contains a container.

A bacterium is provided, which 16S rDNA sequence has at least 85%, at least 90%, at least 95%, at least 96%, at least 97%, at least 98%, at least 99%, at least 99.5% or 100% consistency with a 16S rDNA sequence of *Alistipes*, the bacteria are one or more of active bacteria, inactive bacteria, bacterial derivatives or bacterial metabolites.

A bacterium is provided, which 16S rDNA sequence has at least 99% consistency with a 16S rDNA sequence of *Alistipes finegoldii*, the bacteria are one or more of active bacteria, inactive bacteria, bacterial derivatives or bacterial metabolites.

A bacterium is provided, which 16S rDNA sequence has at least 99.5% or 100% consistency with a 16S rDNA sequence of any of the following strains:

*Alistipes finegoldii* strain deposited at German collection of microorganisms and cell cultures DSMZ (Deutsche Sammlung von Mikroorganismen and Zellkulturen=German collection of microorganisms and cell cultures), under accession number DSM 17242 (NCBI: txid679935, https://www.ncbi.nlm.nih.gov/Taxonomy/Browser/wwwtax.cgi?id=679935);

*Alistipes finegoldii* strain deposited at Japan JCM Culture Collection (Japan Collection of Microorganisms), under accession number JCM 16770;

*Alistipes finegoldii* strain deposited at Korean KCTC Culture Collection (Korean Collection for Type Cultures), with under accession number KCTC 15236;

GDMCC 1.2324, the bacteria are one or more of active bacteria, inactive bacteria, bacterial derivatives or bacterial metabolites.

Preferably, the inactive bacteria are inactive whole-cell bacteria.

Preferably, the active bacteria are intact bacteria and/or intact viable bacteria.

A 16S rDNA sequence of *Alistipes finegoldii* under accession number DSM 17242 (*Alistipes finegoldii* DSM17242) is shown in SEQ ID NO: 1.

```
SEQ ID NO: 1:
agagtttgat cctggctcag gatgaacgct agcggcaggc ttaacacatg caagtcgagg ggcagcgggg agtagcaata ctccgccggc gaccggcgca cgggtgcgta acgcgtatgc aacctacctt taacaggggc ataacactga gaaattggta ctaattcccc ataacattcg agaaggcatc ttcttgggtt aaaaactccg gtggttaaag atgggcatgc gttgtattag ctagttggtg aggtaacggc tcaccaaggc aacgatacat aggggggactg agaggttaac cccccacatt ggtactgaga cacggaccaa actcctacgg gaggcagcag tgaggaatat tggtcaatgg acgcaagtct gaaccagcca tgccgcgtgc aggaagacgg ctctatgagt tgtaaactgc ttttgtacta gggtaaacgc ttttacgtgt aggagcctga aagtatagta cgaataagga tcggctaact ccgtgccagc agccgcggta atacggagga tccaagcgtt atccggattt attgggttta aagggtgcgt aggcggtttg ataagttaga ggtgaaatac cggggctcaa ctccggaact gcctctaata ctgttgaact agagagtagt tgcggtaggc ggaatgtatg gtgtagcggt gaaatgctta gagatcatac agaacaccga ttgcgaaggc agcttaccaa actatatctg acgttgaggc acgaaagcgt ggggagcaaa caggattaga taccctggta gtccacgcag taaacgatga taactcgttg tcggcgatac acagtcggtg actaagcgaa agcgataagt tatccacctg gggagtacgt tcgcaagaat gaaactcaaa ggaattgacg ggggcccgca caagcggagg aacatgtggt ttaattcgat gatacgcgag gaaccttacc cgggcttgaa agttagtgac gattctggaa acaggatttc ccttcggggc acgaaactag gtgctgcatg gttgtcgtca gctcgtgccg tgaggtgtcg ggttaagtcc cataacgagc gcaaccccta ccgttagttg ccatcaggtc aagctgggca ctctggcggg actgccggtg taagccgaga ggaaggtggg gatgacgtca aatcagcacg gcccttacgt ccggggctac acacgtgtta caatggtagg tacagagggc cgctacccg cgaggggatg ccaatctcga aagcctatct cagttcggat cggaggctga aacccgcctc cgtgaagttg gattcgctag taatcgcgca tcagccatgc cgcggtgaat acgttcccgg gccttgtaca caccgcccgt caagccatgg aagctggggg tgcctgaagt tcgtgaccgc aaggagcgac ctagggcaaa accggtgact ggggctaagt cgtaacaagg taaccaa
```

*Alistipes finegoldii* strain deposited at Finland Helsinki Anaerobe Reference Laboratory (Anaerobe Reference Laboratory, Helsinki Collection, National Public health Institute, Helsinki, Finland), under accession number AHN 2437;

*Alistipes finegoldii* strain deposited at Sweden CCUG Culture Collection (Culture Collection University of Gothenburg), under accession number CCUG 46020;

*Alistipes finegoldii* strain deposited at French CIP Culture Collection (Collection de L'Institut Pasteur of Institut Pasteur), under accession number CIP 107999; and

*Alistipes finegoldii* strain deposited at Guangdong Microorganism Culture Collection, under accession number A preparation is provided, wherein an effective amount of two or more of the bacteria for the tumor treatment is added with a pharmaceutically acceptable carrier and an adjuvant to prepare into a freeze-dried powder, a tablet, a capsule, a granule or an injection.

The "pharmaceutically acceptable carrier" refers to a carrier that does not cause significant irritation to organisms and does not interfere with the biological activity and properties of the administered compound. The "adjuvant" refers to a solvent, a diluent or additional excipient, dispersant, and surfactant.

A composition is provided, including any of the bacteria and a pharmaceutically acceptable carrier.

A composition is provided, including any of the bacteria formulated for use as a medicine.

A composition is provided, including any of the bacteria formulated for use as a medical food.

A composition is provided, including a mixture of two or more of any of the bacteria for tumor treatment, and optionally further including a pharmaceutically acceptable carrier.

A composition is provided, including an effective amount of a mixture of two or more of any of the bacteria used for tumor treatment, and optionally further including a pharmaceutically acceptable carrier.

A composition is provided, including an effective amount of two or more of active bacteria, inactive bacteria, bacterial derivatives, or bacterial metabolites of any of the bacteria for tumor treatment, and optionally further including a pharmaceutically acceptable carrier.

A food, beverage, food supplement, probiotic or health food is provided, including any of the bacteria, which is formulated into a preparation for enteral nutrition.

A food, beverage, food supplement, probiotic or health food is provided, including a mixture of two or more of any of the bacteria, which is formulated into a preparation for enteral nutrition.

A bacterium or composition is provided, wherein the bacterium or composition is prepared as a freeze-dried powder, a tablet, a capsule, a granule or an injection.

A bacterium, preparation, composition, foods, beverage, food supplement, probiotic or health food is provided, wherein an administration subject is a human being.

Preferably, the human being is an infant, a child, a teenager, an adult, or an elderly person.

The bacterium, preparation, composition, food, beverage, food supplement, probiotic or health food is administered to a non-human primate, and the non-human primate is a mammal (such as a dog, a cat, a ferret, a horse, a rabbit, a guinea pig, a gerbil, a hamster, a squirrel, a rat, and a mouth); a bird; a reptile; fish; an amphibian; an arthropod or a livestock animal (such as a cattle, a pig, a sheep, a goat, an alpaca, a donkey, a camel, a buffalo or a mink).

It is provided an application of the bacterium, preparation, composition, food, beverage, food supplement, probiotic or health food in tumor treatment.

It is provided an application of the bacterium, preparation, composition, food, beverage, food supplement, probiotic or health food, which includes an effective amount of the bacterium, in tumor treatment.

It is provided an application of the bacterium, preparation, composition, food, beverage, food supplement, probiotic or health food, which includes an effective amount of the bacterium, in the tumor treatment, wherein the bacterium, preparation, composition, food, beverage, food supplement, probiotic or health food is administered in the tumor treatment.

A composition is provided, including an effective amount of any of the bacteria or compositions for cancer treatment, and optionally further including a pharmaceutically acceptable carrier.

A composition is provided, including an effective amount of two or more of any of bacteria or compositions for cancer treatment, and optionally further including a pharmaceutically acceptable carrier.

A composition is provided, including *Alistipes finegoldii* active bacteria and an immune checkpoint inhibitor.

Preferably, the immune checkpoint inhibitor is PD-1 monoclonal antibody (αPD-1) and/or CTLA-4 monoclonal antibody (αCTLA4).

The present invention also provides an application of the composition in preparation of drugs for tumor treatment.

The present invention also provides a medicine, including a composition, specifically, a pharmaceutical composition for tumor treatment with *Alistipes finegoldii* as an active ingredient and an immune checkpoint inhibitor, It is provided an application of one or more of active bacteria, inactive bacteria, bacterial derivatives, or bacterial metabolites of the bacteria belonging to the genus *Alistipes* in preparation of a synergist for an immune checkpoint inhibitor to treat tumors.

Preferably, it is provided an application of *Alistipes finegoldii* as an active ingredient in preparation of a synergist for an immune checkpoint inhibitor.

More preferably, the administration of *Alistipes finegoldii* is one of or a combination of more of following strains:

*Alistipes finegoldii* strain deposited at German collection of microorganisms and cell cultures DSMZ, under accession number DSM 17242 (NCBI: txid679935, https://www.ncbi.nlm.nih.gov/Taxonomy/Browser/wwwtax.cgi?id=679935);

*Alistipes finegoldii* strain deposited at JCM Japan Collection of Microorganisms (Deutsche Sammlung von Mikroorganismen and Zellkulturen=German collection of microorganisms and cell cultures), under accession number JCM 16770;

*Alistipes finegoldii* strain deposited at KCTC Korean Collection for Type Cultures, with under accession number KCTC 15236;

*Alistipes finegoldii* strain deposited at Finland Helsinki Anaerobe Reference Laboratory (Anaerobe Reference Laboratory, Helsinki Collection, National Public health Institute, Helsinki, Finland), under accession number AHN 2437;

*Alistipes finegoldii* strain deposited at Sweden CCUG Culture Collection (Culture Collection University of Gothenburg), under accession number CCUG 46020;

*Alistipes finegoldii* strain deposited at French CIP Culture Collection (Collection de L'Institut Pasteur of Institut Pasteur), under accession number CIP 107999; and

*Alistipes finegoldii* strain deposited at Guangdong Microorganism Culture Collection, under accession number GDMCC 1.2324.

The present invention provides *Alistipes finegoldii* (Af) for treating tumor patients, which potentiates immune checkpoint inhibitors. Specifically, the present invention proposes a combination therapy: an immune checkpoint inhibitor treatment will be performed simultaneously, separately or sequentially with the administration of active and inactive whole-cell Af, thereby promoting the therapeutic effect of the immune checkpoint inhibitor.

Gut inherent microbiota are eliminated before administration of *Alistipes finegoldii*.

Gut inherent microbiota are eliminated with an antibiotic combination.

Gut inherent microbiota are eliminated with an antibiotic combination, treated for 7 days.

Antibiotic combination: metronidazole 100 mg/kg, vancomycin 50 mg/kg, penicillin sodium 100 mg/kg, and neomycin sulfate 100 mg/kg.

An administration mode of Af is oral administration.

An administration sequence of the combination therapy is: Af is administered simultaneously, before and/or after an immune checkpoint inhibitors therapy is performed.

In the combination therapy, according to tolerance of an individual patient to the treatment, dose delay and/or dose reduction and time adjustment are performed as needed.

The Af in the present invention may include an effective amount of *Alistipes finegoldii* usually dispersed in a pharmaceutically or pharmacologically acceptable carrier.

The term "pharmaceutically or pharmacologically acceptable" refers to molecular entities and compositions that do not produce adverse reactions, allergic reactions, or other adverse reactions when administered to animals (e.g., human beings, if appropriate). Specific examples of the pharmacologically acceptable carriers as described herein are a borate buffer solution or a sterile saline solution.

The synergistic immune checkpoint inhibitors of the present invention can be used for the patients refractory to immune checkpoint inhibitors, wherein the patients refractory to immune checkpoint inhibitors exhibit congenital (primary) resistance to the immune checkpoint inhibitor treatment, which is manifested as lack of or insufficience of responses to the checkpoint inhibitor treatment lasting for at least about 8 or 12 weeks from the first dose.

The synergistic immune checkpoint inhibitor of the present invention can be used for patients refractory to immune checkpoint inhibitors, wherein the patients refractory to immune checkpoint inhibitors exhibit acquired (secondary) resistance to the immune checkpoint inhibitor treatment, which is manifested as that there is an initial response to the checkpoint treatment, but one or more tumors subsequently relapse and develop.

In a therapeutic effect evaluation of the combination therapy described in the present invention the enhanced therapeutic effect is measured by the increased overall survival time.

In the therapeutic effect evaluation of the combination therapy described in the present invention, the enhanced therapeutic effect is measured by the increased progression free survival.

In the therapeutic effect evaluation of the combination therapy described in the present invention, wherein as defined by RECIST 1.1, the enhanced therapeutic effect is measured by the tumor size of one or more of the tumors reduced or stabilized, including disease stabilization (SD), complete remission (CR) or partial remission (PR) of the target tumor; and/or disease stabilization (SD) or complete remission (CR) of one or more non-target tumors.

In the therapeutic effect evaluation of the combination therapy described in the present invention, the enhanced therapeutic effect is measured by the improved overall remission rate and/or the improved life quality.

In a safety evaluation of the combination therapy described in the present invention, the safety is measured by whether diarrhea or enteritis is caused.

Compared with the prior art, the present invention has the following beneficial effects.

The present invention uses a monobacterial oral preparation of human commensal bacteria, combined with an immune checkpoint inhibitor, and an anti-tumor immune protective response is generated by bacterial stimulation, which significantly enhances an efficacy of the immune checkpoint inhibitors on multiple species of tumors, and has better safety, prolongs overall survival time of cancer patients, increases response rate of the cancer immunotherapy population, and expands cancer patient population benefited from cancer immunotherapy (immunotherapy checkpoint inhibitors).

DETAILED DESCRIPTION

Figure 1:
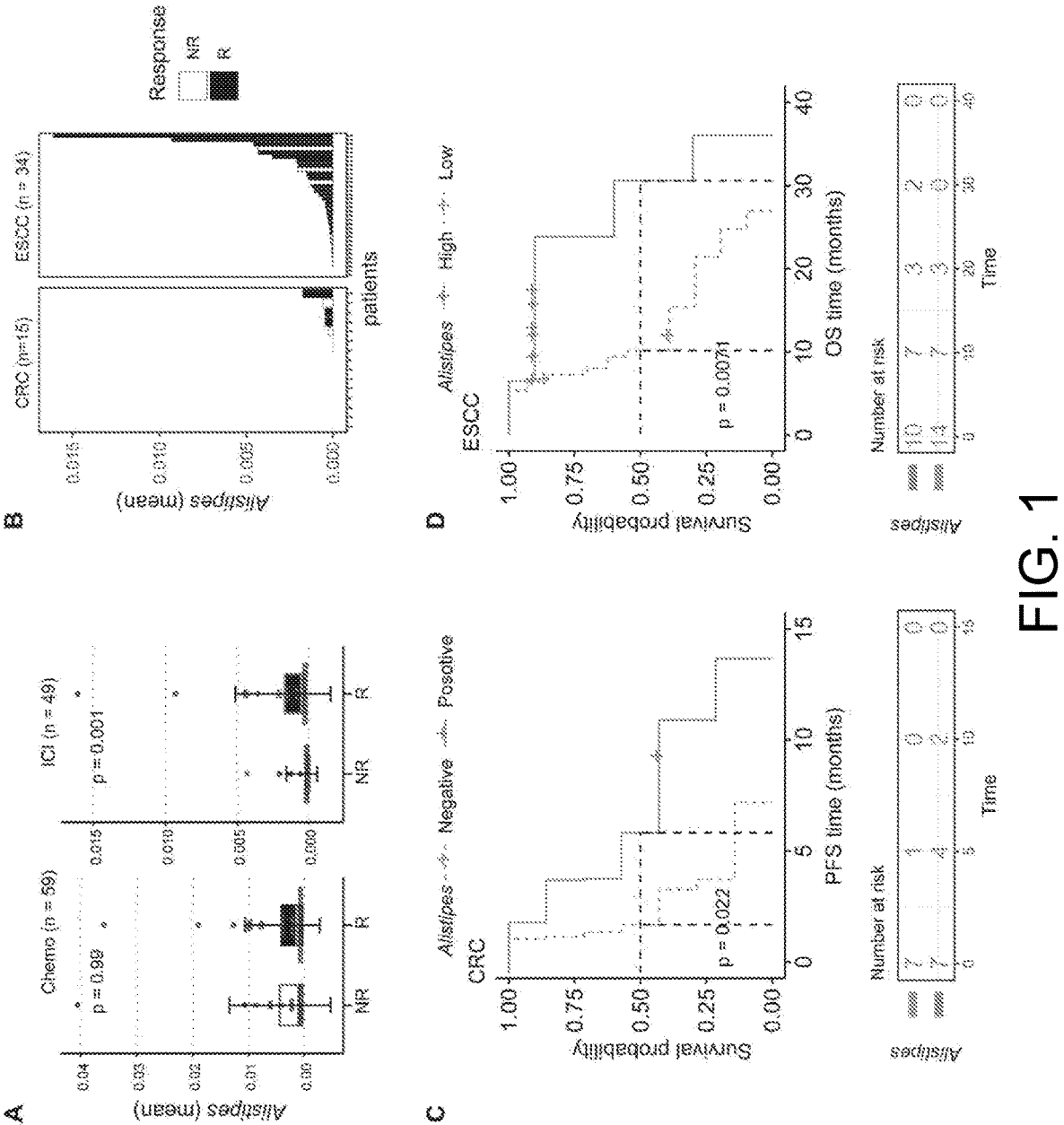
FIG. 1 shows use of clinical cohorts to screen gut microbiota that can promote immune checkpoint inhibitors in Embodiment 1.

The present invention will be further described in detail below in conjunction with the accompanying drawings of the description and specific embodiments. The embodiments are only used to explain the present invention and are not used to limit the scope of the present invention. The test methods used in the following embodiments are conventional methods unless otherwise specified; the materials and reagents used, unless otherwise specified, are commercially available reagents and materials.

Embodiment 1 Use of Clinical Cohort to Screen Gut Microbiota that can Potentiate Immune Checkpoint Inhibitors I. Experimental Methods 1. Datasets (1) Gut microbiota were obtained from 230 feces samples at different time points after treatment in 108 colorectal cancer (CRC) or esophageal cancer (ESCC) patients. Among them, 115 samples were from immune checkpoint inhibitor group (ICI) patients whose treatment method was anti-PD1 antibody therapy combined with chemotherapy or combined with targeted drugs, and 115 samples were from chemotherapy group (Chemo) patients (Table 1). Efficacy-related assessments mainly include progression-free survival (PFS), survival (OS), and optimal efficacy. We defined patients with the optimal efficacy of complete remission (CR) and partial response (PR) as treatment responder patients (R), and patients with the optimal efficacy of stable disease (SD) and progressive disease (PD) as treatment non-responder patients (NR).

TABLE 1

Baseline characteristics of patients in the clinical cohort

| name | levels | Chemo (N = 59) | ICI (N = 49) | p |
|---|---|---|---|---|
| Tumor | CRC | 40 (67.8%) | 15 (30.6%) | <.001 |
| | ESCC | 19 (32.2%) | 34 (69.4%) | |
| Gender | Female | 15 (25.4%) | 10 (20.4%) | .699 |
| | Male | 44 (74.6%) | 39 (79.6%) | |
| Age | Mean ± SD | 57.7 ± 8.1 | 55.8 ± 9.9 | 272 |
| BMI | Mean ± SD | 22.2 ± 3.1 | 22.3 ± 3.3 | 832 |
| PFStime | <6 m | 19 (32.2%) | 24 (57.1%) | .022 |
| | >6 m | 40 (67.8%) | 18 (42.9%) | |
| Response | NR | 20 (33.9%) | 19 (38.8%) | .746 |
| | R | 39 (66.1%) | 30 (61.2%) | |

(2) DNA was extracted from 115 feces samples, and V3-V4 region of the 16S rRNA gene was amplified and sequenced (Illumina HiSeq platform). 16S rRNA sequencing data analysis was performed using USEARCH software (version 11.0.667) for quality control, filtering and species identification. If a patient included feces samples from multiple post-treatment time points, the species abundances of the gut microbiota were averaged at different time points for subsequent analysis. In order to enable the analysis results to be verified by pure culture experiments at a strain level, the LTP (Living Tree Project) database was used for species identification. The LTP database primarily collects sequences of typical strains and isolates classified according to observed traits. In order to improve the accuracy of 16S rRNA sequencing for species-level bacterial identification as much as possible, the SINTAX algorithm was used for species annotation, the algorithm can score and rank the identified species with confidence level, and screen the intestinal bacteria whose species annotation confidence level is greater than 75% for further analysis.

2. Statistical Analysis (1) Univariate cox regression analysis of PFS and OS: All bacteria at a genus level of the gut microbiota were subjected to univariate cox regression analysis using the R language package survival (version number: 3.3-1).

(2) Difference analysis between groups: Wilcoxon rank-sum test was used to analyze statistical differences between groups.

II. Experimental Results

FIG. 1A shows mean relative abundances of *Alistipes* in the gut at different time points after treatment in Chemo and ICI responder patients (R) and non-responder patients (NR). In the ICI group, the mean relative abundance of intestinal *Alistipes* in the R group patients after treatment was significantly higher than that in the NR group patients (p<0.001), while in the Chemo group, the mean relative abundance of intestinal *Alistipes* in the R group patients after treatment was significantly higher than that in the NR group patients (p<0.001). There was no significant difference between patients in the NR group (p=0.99). This indicated that the higher abundance of *Alistipes* after treatment was associated with better efficacy of immune checkpoint inhibitors. FIG. 1B shows mean relative abundances of *Alistipes* in the gut of CRC and ESCC patients at different time points after receiving immune checkpoint inhibitors.

The results showed that *Alistipes* showed zero value in 50% of CRC patients after receiving immune checkpoint inhibitors, while *Alistipes* could be detected in all ESCC patients. Therefore, we divided CRC patients into two groups: Negative (relative abundance of *Alistipes* equal to zero) and Positive (relative abundance of *Alistipes* greater than zero) according to whether the mean relative abundance of *Alistipes* after receiving immune checkpoint inhibitor treatment was zero; ESCC patients were divided into two groups, High (greater than or equal to mean) and low (less than mean) according to the mean relative abundances of *Alistipes* after receiving immune checkpoint inhibitor treatment.

FIG. 1C shows a comparison of Kaplan-Meier (KM) curves of progression-free survival (PFS) of CRC patients in Negative group and Positive group. FIG. 1D shows a comparison of Kaplan-Meier (KM) curves of overall survival (OS) of ESCC patients in High group and low group. The results showed that the PFS of CRC patients in Positive group was significantly longer than that in Negative group (log-rank p=0.02); ESCC patients with high mean relative abundance of *Alistipes* had significantly longer overall survival than patients with low mean relative abundance of *Alistipes* (log-rank p=0.0071).

These data suggest that the higher abundance of *Alistipes* in the gut after receiving immune checkpoint inhibitors is beneficial for the efficacy of immune checkpoint inhibitors.

Figure 2:
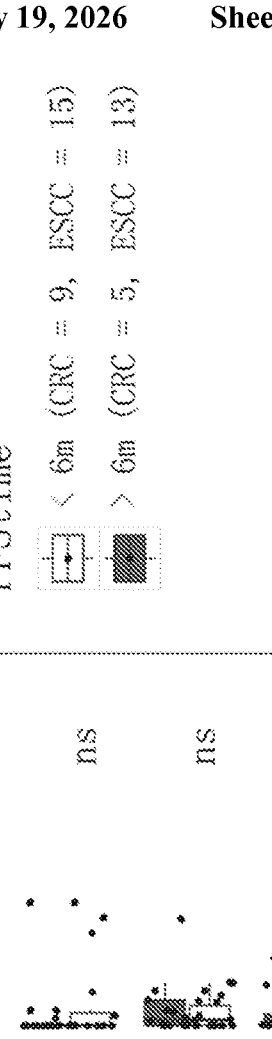
FIG. 2 shows relationship between different *Alistipes* species and therapeutic efficacy of immune checkpoint inhibitors in the clinical cohorts of Embodiment 1.
Figure 2:
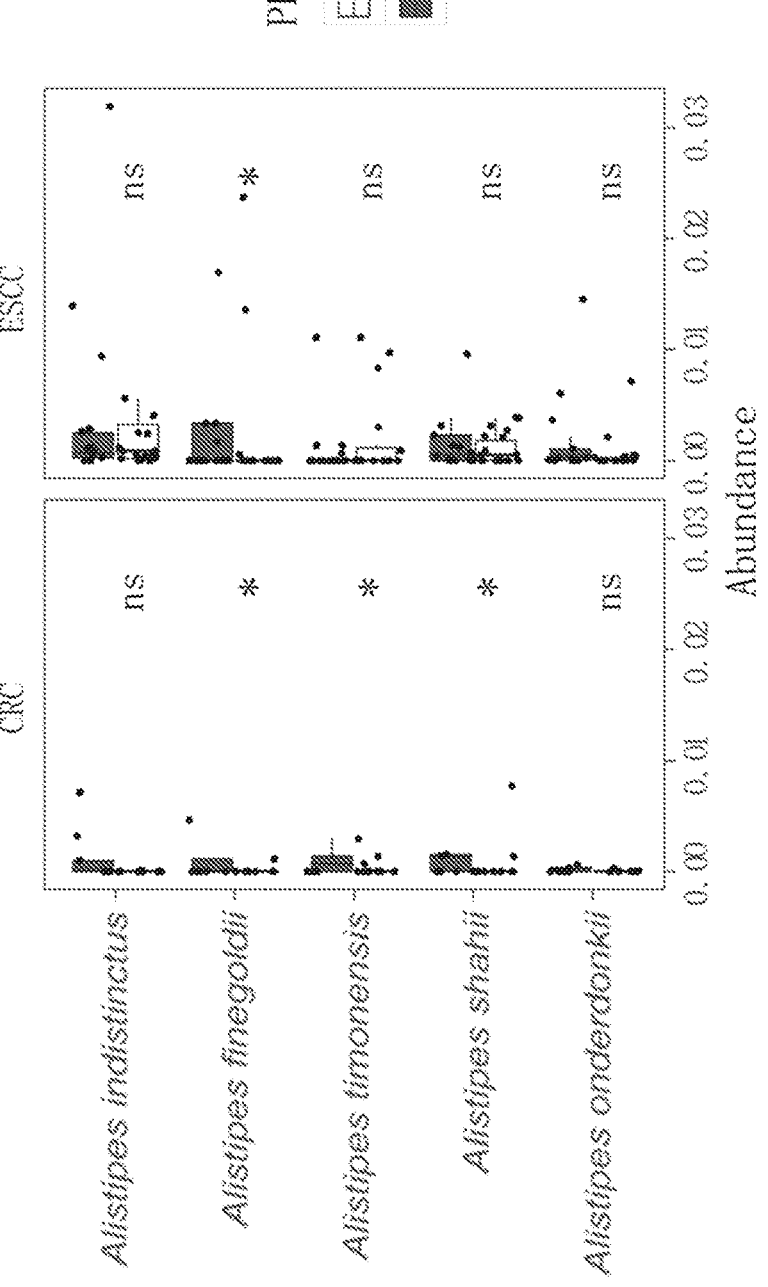

FIG. 2 is an analysis of the relationship between different *Alistipes* strains and immune checkpoint inhibitor treatment efficacy time. In this dataset, a total of 11 OTUs (Operational Taxonomic Units) belonging to *Alistipes* with a confidence level greater than 0.75 were compared, involving 5 *Alistipes* species, including 1 *Alistipes finegoldii,* 4 *Alistipes indistinctus,* 3 *Alistipes onderdonkii,* 2 *Alistipes shahii* and 1 *Alistipes timonensis,* of which Otu1557 was identified as *Alistipes finegoldii* with 98% confidence level (Table 2).

Among the 5 *Alistipes* species detected, the relative abundances of *Alistipes finegoldii, Alistipes timonensis* and *Alistipes shahii* in the gut of CRC patients with PFS greater than 6 months after receiving αPD-1 combined with chemotherapy were significantly higher than those of patients with PFS less than 6 months. The relative abundance of *Alistipes finegoldii* in the gut of ESCC and CRC patients with PFS greater than 6 months after receiving αPD-1 combined with chemotherapy was significantly higher than that of patients with PFS less than 6 months. The results show that *Alistipes finegoldii* may have a broader spectrum of potentiating immune checkpoint inhibitors than other *Alistipes* species.

TABLE 2

Alistipes species detected in the clinical
cohort and their confidence levels

| OtuID | SINTAX annotation (bootstrap confidence values) |
|---|---|
| Otu1557 | f: Rikenellaceae(1.0000), g: *Alistipes*(1.0000), s: *Alistipes_finegoldii*(0.9800) |
| Otu150 | f: Rikenellaceae(1.0000), g: *Alistipes*(1.0000), s: *Alistipes_indistinctus*(1.0000) |
| Otu194 | f: Rikenellaceae(0.9900), g: *Alistipes*(0.9801), s: *Alistipes_indistinctus*(0.8919) |
| Otu379 | f: Rikenellaceae(1.0000), g: *Alistipes*(1.0000), s: *Alistipes_indistinctus*(0.9800) |
| Otu942 | f: Rikenellaceae(0.9700), g: *Alistipes*(0.9215), s: *Alistipes_indistinctus*(0.8201) |
| Otu14 | f: Rikenellaceae(1.0000), g: *Alistipes*(1.0000), s: *Alistipes_onderdonkii*(1.0000) |
| Otu1388 | f: Rikenellaceae(1.0000), g: *Alistipes*(1.0000), s: *Alistipes_onderdonkii*(0.8400) |
| Otu2345 | f: Rikenellaceae(0.9800), g: *Alistipes*(0.9604), s: *Alistipes_onderdonkii*(0.9028) |
| Otu151 | f: Rikenellaceae(1.0000), g: *Alistipes*(1.0000), s: *Alistipes_shahii*(0.9100) |
| Otu365 | f: Rikenellaceae(1.0000), g: *Alistipes*(1.0000), s: *Alistipes_shahii*(0.7800) |
| Otu450 | f: Rikenellaceae(1.0000), g: *Alistipes*(1.0000), s: *Alistipes_timonensis*(0.9000) |

Embodiment 2 Comparison of Efficacy of Different Active *Alistipes* Strains Alone or a Combination of Active *Alistipes* Strains to Potentiate Immune Checkpoint Inhibitors I. Experimental Methods 1. Experimental Materials (1) Mouse: 6-week-old female C57BL/6J mice (2) Tumor cell lines: murine melanoma cell line (B16-OVA, ATCC), murine colon cancer cell line (MC38, ATCC)

(3) *Alistipes* species (*Alistipes*.sp), selected from:

*Alistipes finegoldii* (DSM No.: 17242, Type strain, which 16S rDNA sequence is shown in SEQ ID NO: 1), referred to as Af, commercially purchased from German collection of microorganisms and cell cultures DSMZ (official website of DSMZ: http://www.dsmz.de).

*Alistipes shahii* (DSM No.: 19121, Type strain), referred to as As, commercially purchased from German collection of microorganisms and cell cultures DSMZ.

(4) Bacterial culture medium: liquid DSMZ104 culture medium, which formula mainly includes peptone, yeast extract, beef extract and glucose, etc., commercially purchased from German collection of microorganisms and cell cultures DSMZ.

(5) Immune checkpoint inhibitors: PD-1 monoclonal antibody (αPD-1), clone number G4C2, the reagent was presented by Shanghai Junshi Biomedical Technology Co., Ltd.

(6) Antibiotic combination: metronidazole 100 mg/kg, vancomycin 50 mg/kg, penicillin sodium 100 mg/kg, and neomycin sulfate 100 mg/kg 2. Experimental Grouping The experimental grouping is shown in Table 3.

TABLE 3

Experimental grouping

| Cell line | Group | Mouse quantity | Dose (each) | Times of frequency | Frequency of treatment |
|---|---|---|---|---|---|
| MC38 | IgG | 6 | 200 μg | 3 times | every two days |
| | IgG + *Alistipes*. sp | 6 | IgG: 200 μg, *Alistipes*. sp: $1 \times 10^9$ CFU | IgG for 3 times, *Alistipes*. sp for 6 times | IgG every two days, *Alistipes*. sp every one day |
| | αPD-1 | 6 | 200 μg | 3 times | every two days |
| | αPD-1 + *Alistipes*. sp | 6 | αPD-1: 200 μg, *Alistipes*. sp: $1 \times 10^9$ CFU | αPD-1 for 3 times, *Alistipes*. sp for 6 times | αPD-1 every two days, *Alistipes*. sp every one day |
| B16-OVA | IgG | 6 | 200 μg | 3 times | every two days |
| | IgG + *Alistipes*. sp | 6 | IgG: 200 μg, *Alistipes*. sp: $1 \times 10^9$ CFU | IgG for 3 times, *Alistipes*. sp for 6 times | IgG every two days, *Alistipes*. sp every one day |
| | αPD-1 | 6 | 200 μg | 3 times | every two days |
| | αPD-1 + *Alistipes*. sp | 6 | αPD-1: 200 μg, *Alistipes*. sp: $1 \times 10^9$ CFU | αPD-1 for 3 times, *Alistipes*. sp for 6 times | αPD-1 every two days, *Alistipes*. sp every one day |

*Alistipes*. sp = 1) Af: *Alistipes finegoldii*; 2) As: *Alistipes shahii*; 3) Af + As: *Alistipes finegoldii* + *Alistipes shahii*

Figure 3:
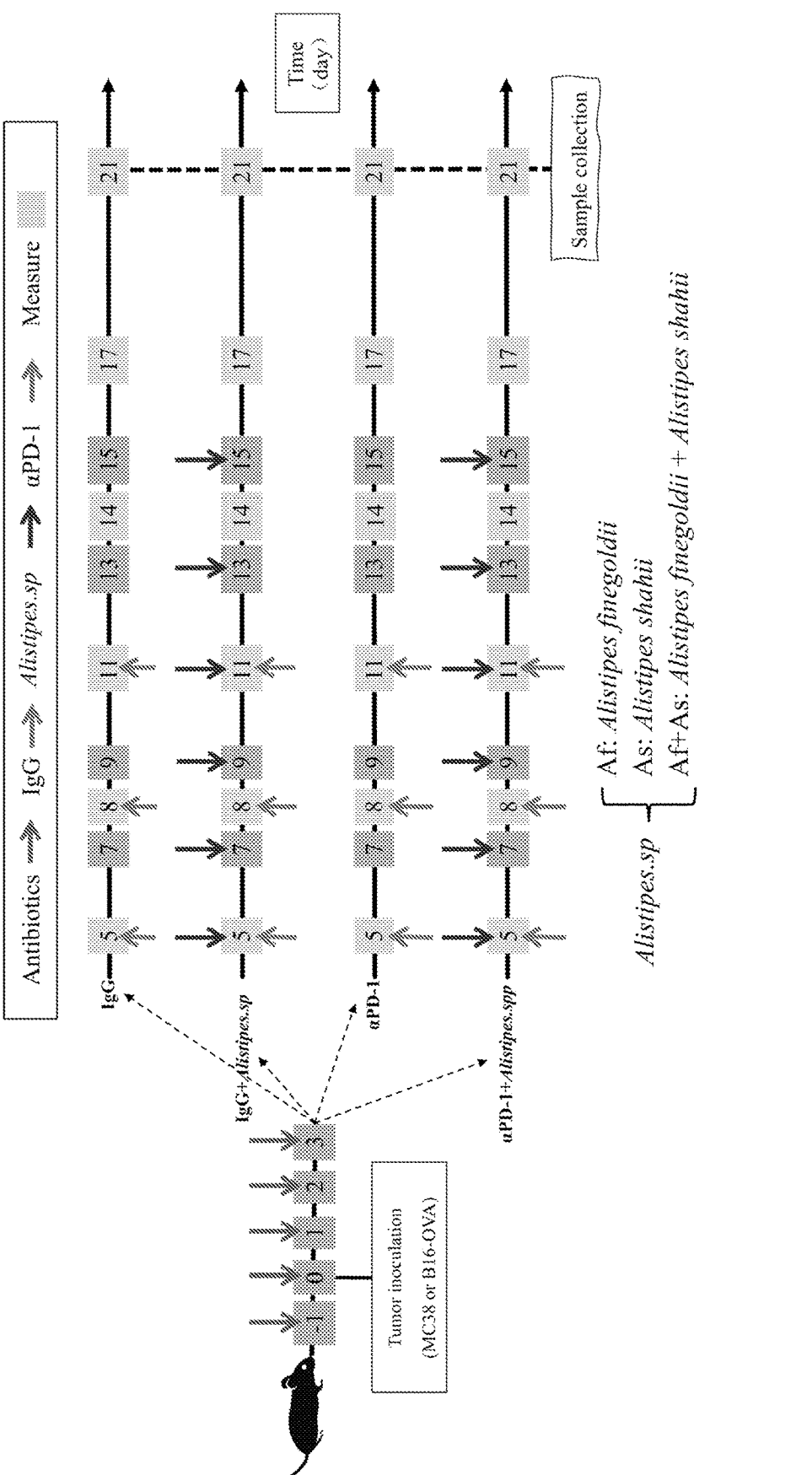
FIG. 3 is a flowchart of administration of different active *Alistipes* species in mouse models of colon cancer and melanoma in Embodiment 2.

3. Experimental Steps (Process Shown in FIG. 3)

(1) Active *Alistipes* species cultivation: *Alistipes* species (Af, As or Af+As) was inoculated in DSMZ104 liquid medium, cultured in an anaerobic chamber at 37° C. for 18 hours, and then centrifuged to a concentration of $1\times10^{10}$ CFU/ml.

(2) Tumor cells were inoculated subcutaneously, MC38 cells $1\times10^6$/mouse, B16-OVA cells $5\times10^5$/mouse.

(3) Day 1 to Day 3: the antibiotics combination was administered by gavage to each group of mice to eliminate gut inherent microbiota.

(4) On Day 5, Day 8 and Day 11 respectively, IgG or αPD-1 was injected intraperitoneally, 200 μg/mouse.

(5) On Day 5, Day 7, Day 9, Day 11, Day 13, and Day 15 respectively, active *Alistipe* species were administered by gavage for treatment, 100 μl/mouse, dosage of monobacterial Af or As is: $1\times10^9$ CFU/mouse. A combined dosage of Af+As is: Af: $0.5\times10^9$ CFU+As: $0.5\times10^9$ CFU/mouse.

(6) On Day 5, Day 8, Day 11, Day 14, Day 17 and Day 21 respectively, a tumor size was measured and a tumor volume was calculated.

$$\text{Tumor volume} = \frac{\text{tumor width}^2 \times \text{tumor length}}{2}$$

(7) The mice were euthanized on Day 21, tumor tissues were taken out, photographed and weighed, and intestinal tissues were taken for HE staining to confirm enteritis condition.

The mouse tumor volume was measured, the tumor weight at the endpoint was measured, an immunohistochemical evaluation was used to evaluate effect of immune cell infiltration in tumor tissues.

Mouse anal and intestinal tissue sections stained with HE were used to observe and evaluate whether *Alistipes finegoldii* would cause enteritis for safety evaluation.

Flow cytometry was used to detect tumor-killing-associated immune cells in mouse blood to assess systemic anti-tumor immune responses.

II. Experimental Results

Figure 4:
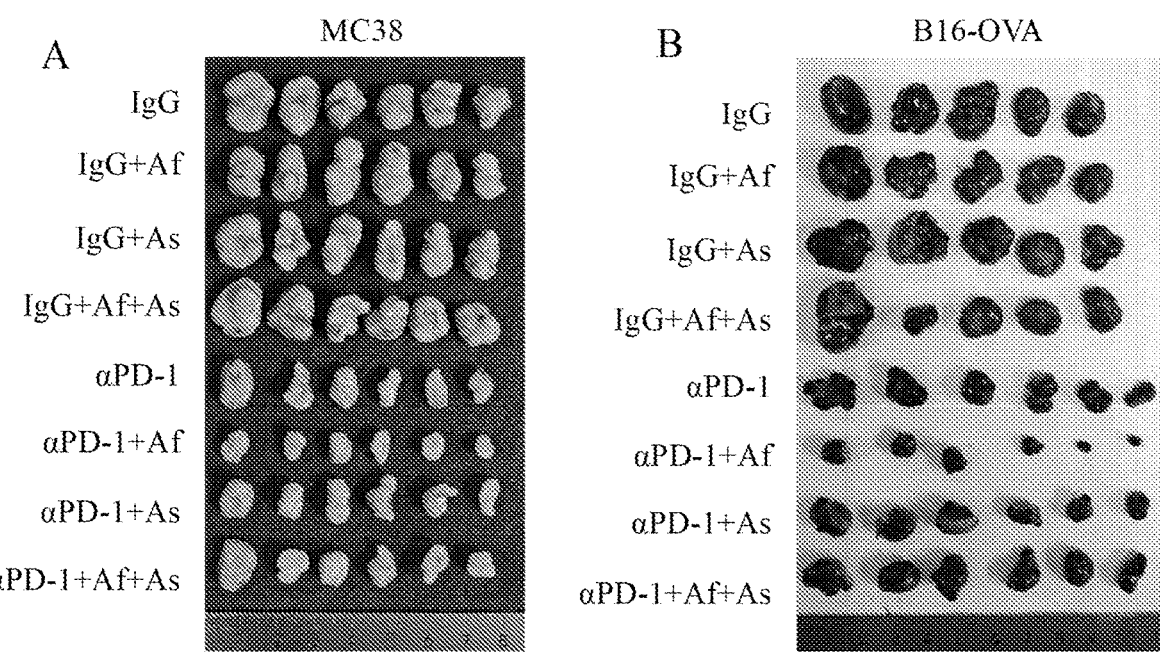
FIG. 4 is a tumor image (Day 21) in Embodiment 2.
Figure 5:
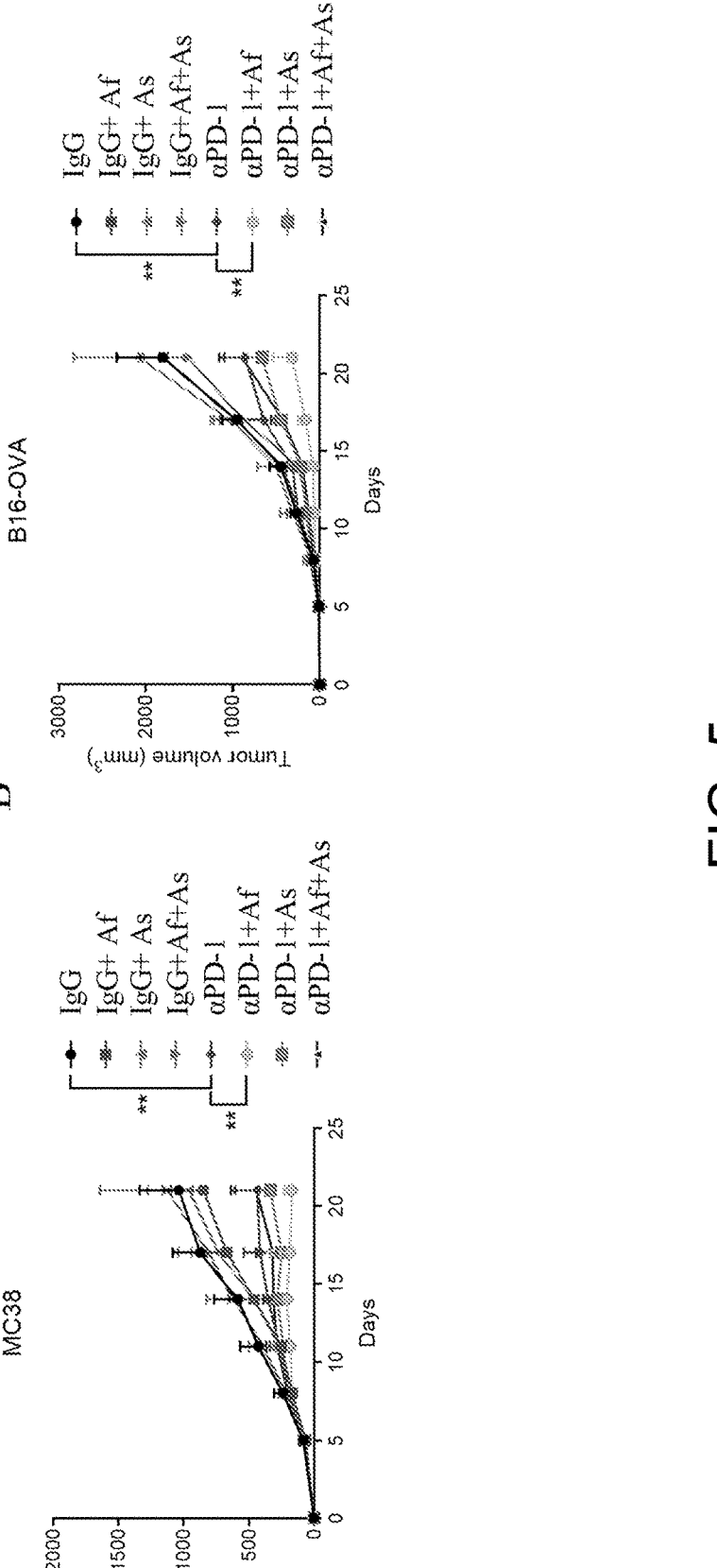
FIG. 5 is a change curve in tumor volume in Embodiment 2.
Figure 6:
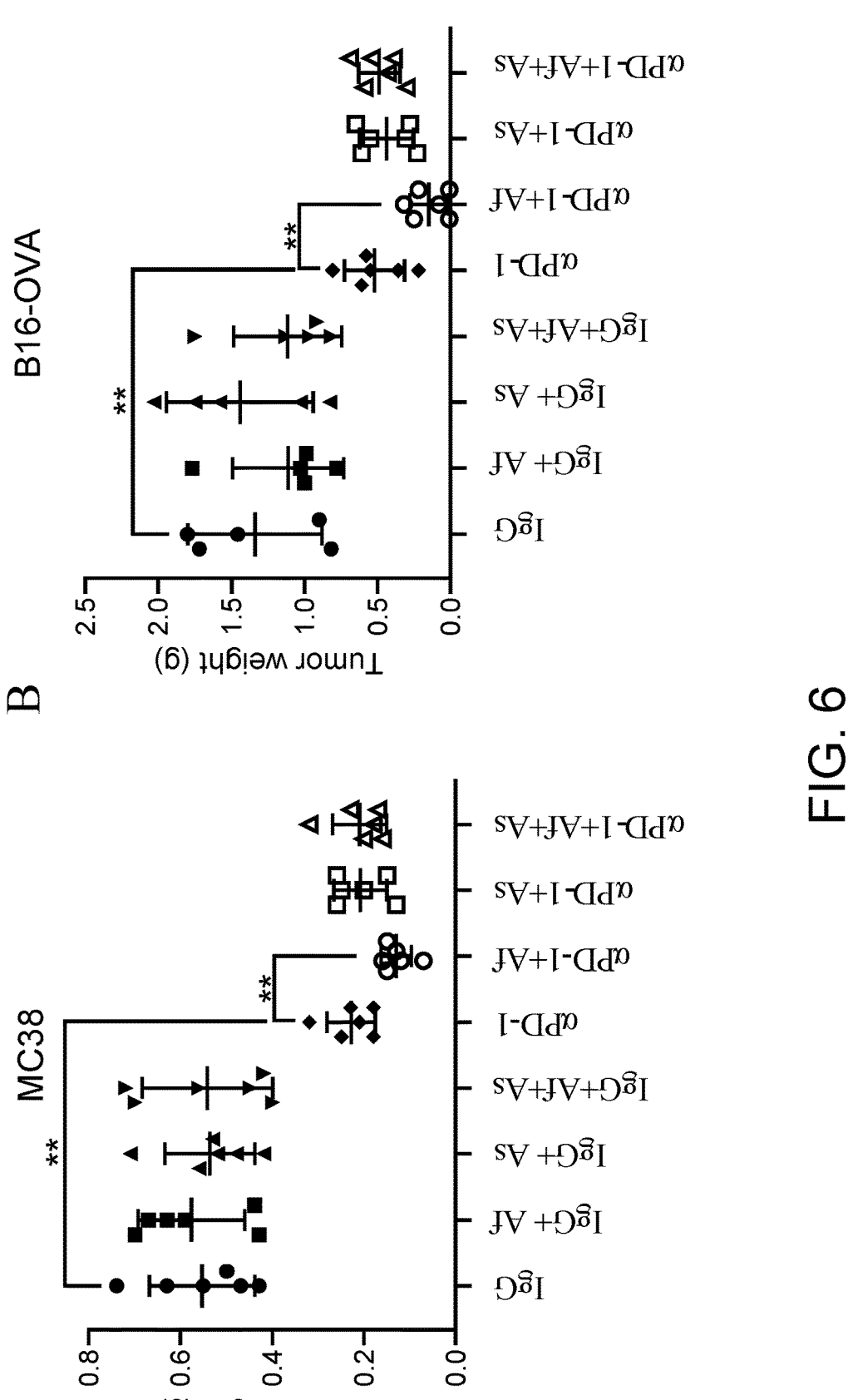
FIG. 6 is a statistics graph of tumor weight in Embodiment 2.

FIG. 4 shows the tumors on Day 21, FIG. 5 is the change curve in tumor volume and FIG. 6 is the statistics graph of tumor weight. In a MC38 colon cancer and B16-OVA melanoma mouse models, compared with non-treatment group (IgG), monotherapy group (αPD-1) shows obvious and significant (p<0.01) tumor reduction. Compared with the monotherapy group (αPD-1), only active Af combination therapy group (αPD-1+Af) shows significant (p<0.01) tumor reduction, however there was no statistical difference between active As combination therapy group (αPD-1+As) and active Af+As combination therapy group (αPD-1+Af+As) and monotherapy group (αPD-1).

It proves that *Alistipes finegoldii* can enhance the anti-tumor effect of αPD-1. However, *Alistipes shahii* as well as combination of *Alistipes shahii* and *Alistipes finegoldii* (Af+As) could not enhance the anti-tumor effect of αPD-1.

In addition, there is no difference between the tumors of mice in the *Alistipes finegoldii* mono active bacterium treatment group (IgG+Af) and the non-treatment group (IgG), indicating that the anti-tumor effect of *Alistipes finegoldii* depends on αPD-1.

Figure 7:
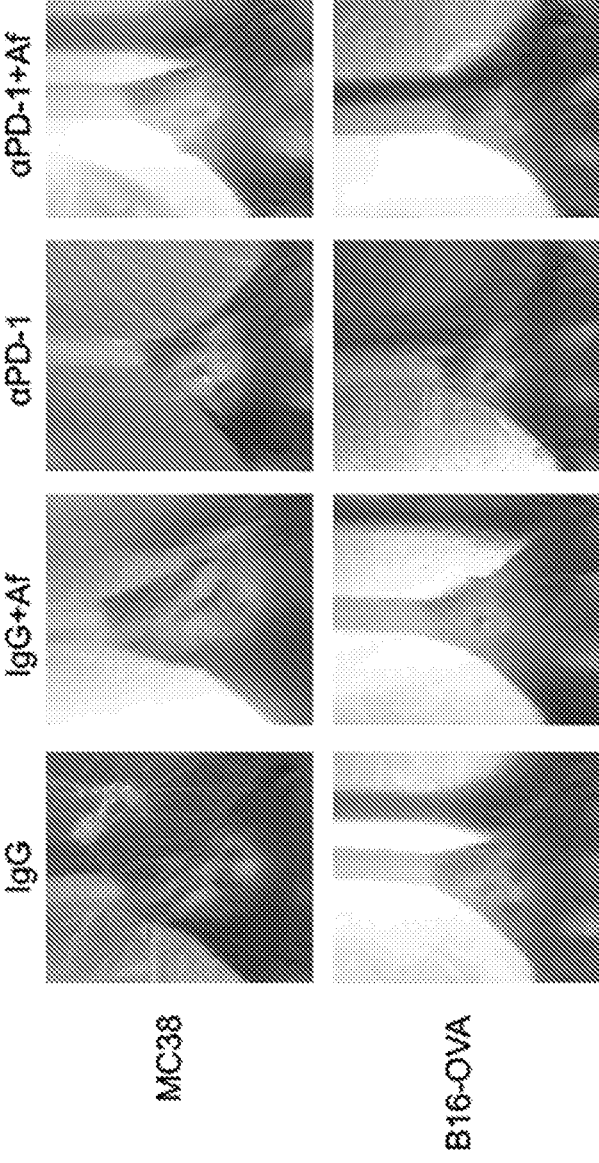
FIG. 7 is an image of mouse anus (Day 21) in Embodiment 2.
Figure 8:
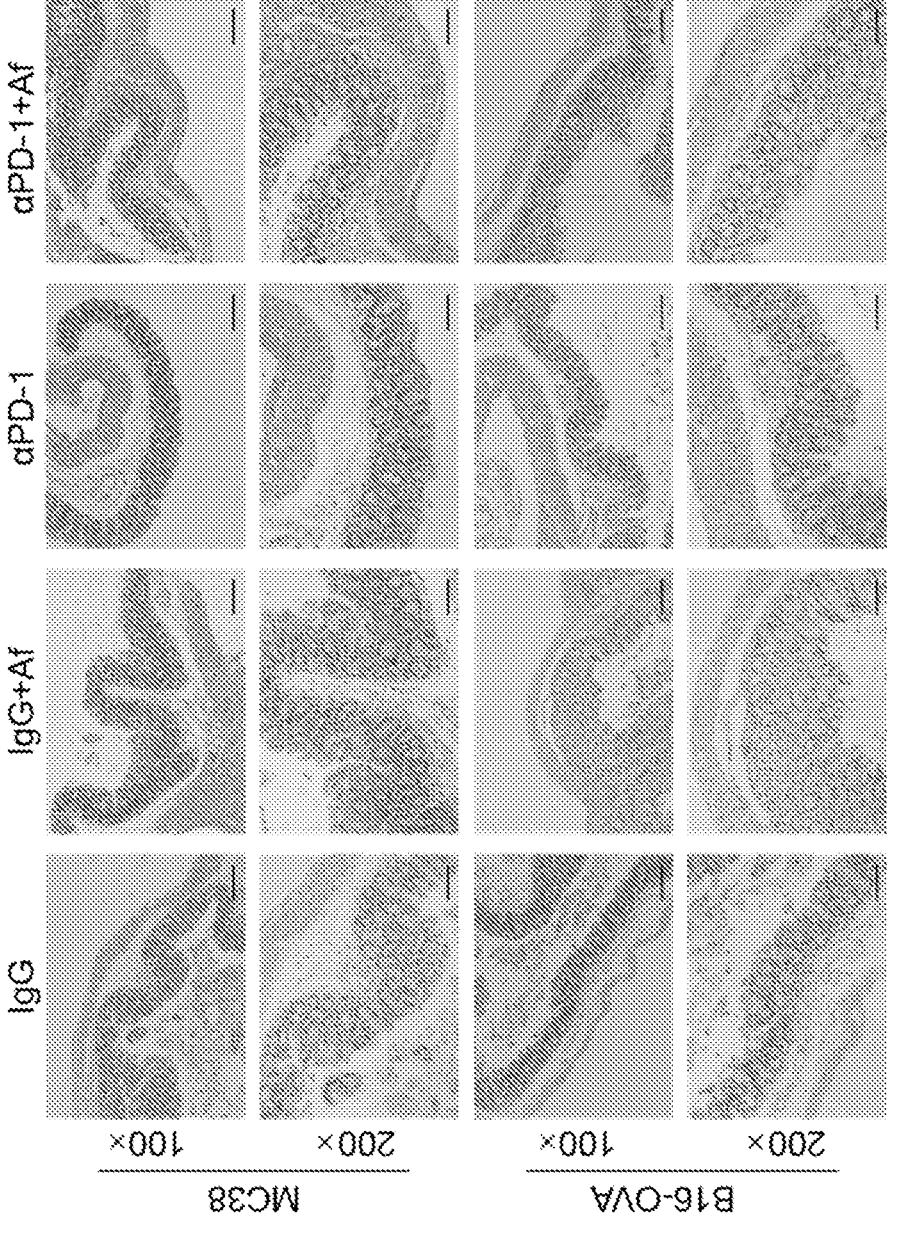
FIG. 8 is a HE staining image of mouse intestinal tissues (Day 21) in Embodiment 2.

The images of mouse anus in FIG. 7 and the HE staining images of the intestinal tissue section in FIG. 8 show that the mice in the mono active Af therapy group (IgG+Af) and the Af combination therapy group (αPD-1+Af) are not found to have enteritis, which proves the safety of *Alistipes finegoldii* via gastrointestinal administration.

Figure 9:
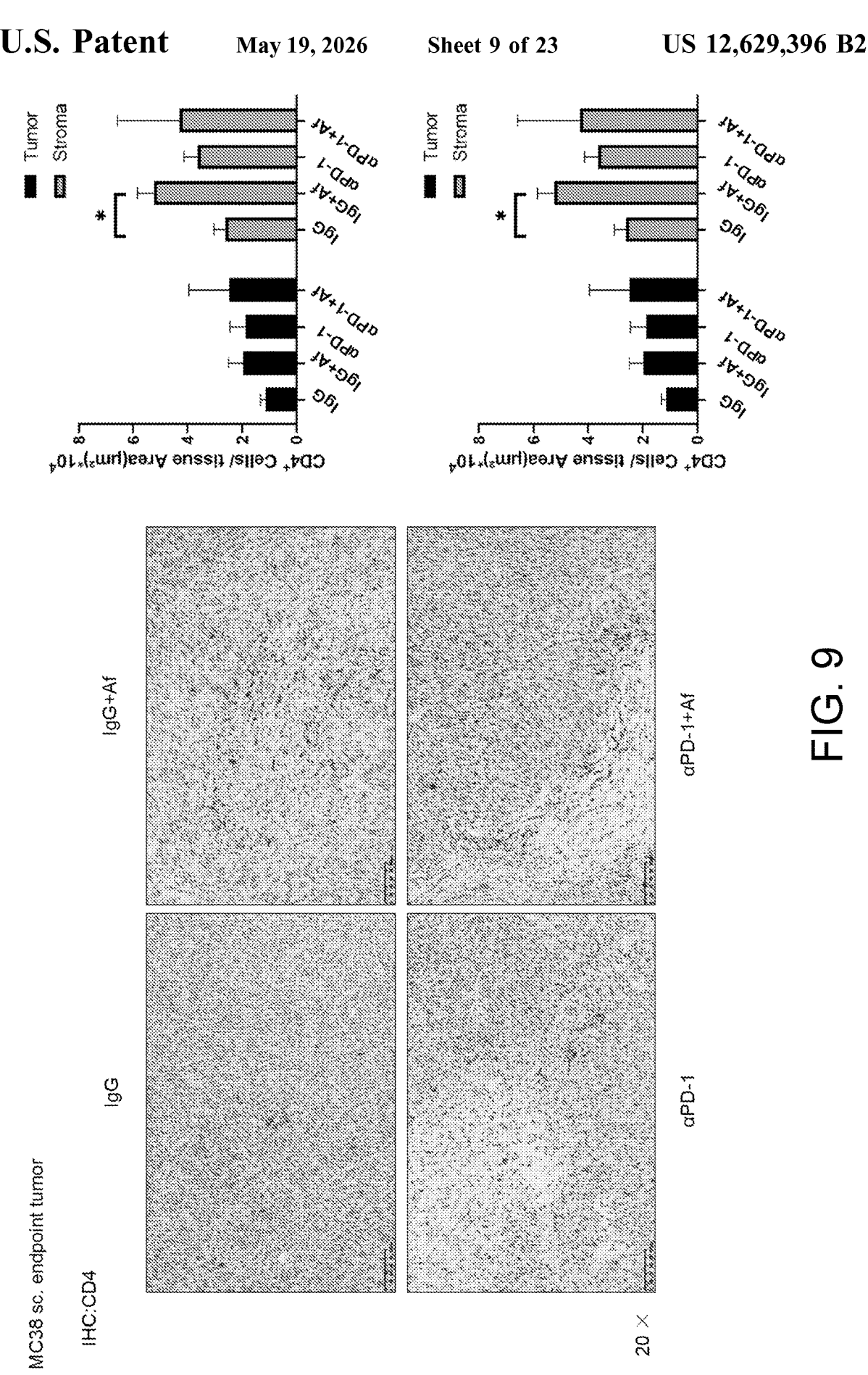
FIG. 9 is an immunohistochemical image of tumor tissue immune cells (Day 21) in Embodiment 2.

Immunohistochemistry of the tumor tissue of the MC38 mouse model at the experiment end in FIG. 9 shows that the active Af combination therapy group (IgG+Af) could significantly increase the infiltration of CD4+ T helper cell in the interstitial area of the tumor; compared with the monotherapy group (αPD-1), the active Af combination therapy group (αPD-1+Af) shows an increased trend of CD4+ T helper cell infiltration in the tumor interstitial area, but does not reach a statistical difference. Compared with the non-treatment group (IgG), the CD4+ T helper cell infiltration of the monotherapygroup (αPD-1) at the end point of mouse experiment only has an increased trend, but does not reach a statistical difference. This result shows that the effect of monotherapy (αPD-1) and active Af combination therapy (αPD-1+Af) on immune cell infiltration in mouse tumor tissue may be short-term, and no significant difference can be detected in the tumor samples at the end of the experiment. The effect of *Alistipes finegoldii* mono active bacterium treatment (IgG+Af) on immune cell infiltration in mouse tumor tissue lasts for a longer time, and there is still a significant increase in CD4+ T helper cell infiltration after the treatment is stopped for one week, which proves oral administration of *Alistipes finegoldii* monobacterium has a regulatory effect on tumor immune microenvironment.

Figure 10:
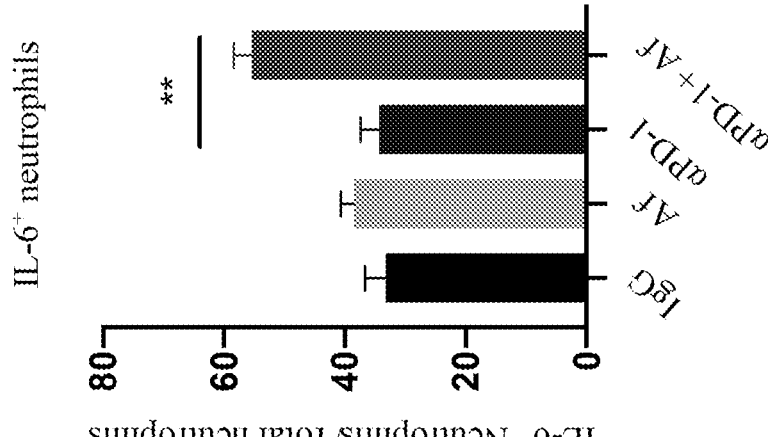
FIG. 10 shows tumor-killing related immune-protective responses after administration of *Alistipes finegoldii* by flow cytometry in Embodiment 2.
Figure 10:
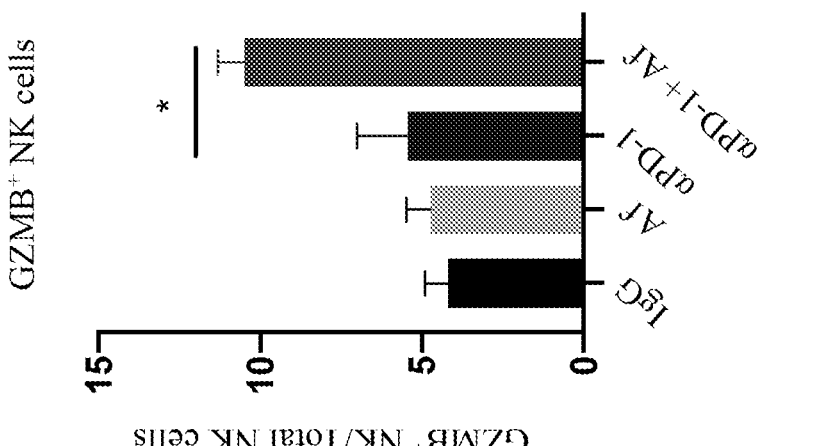
Figure 10:
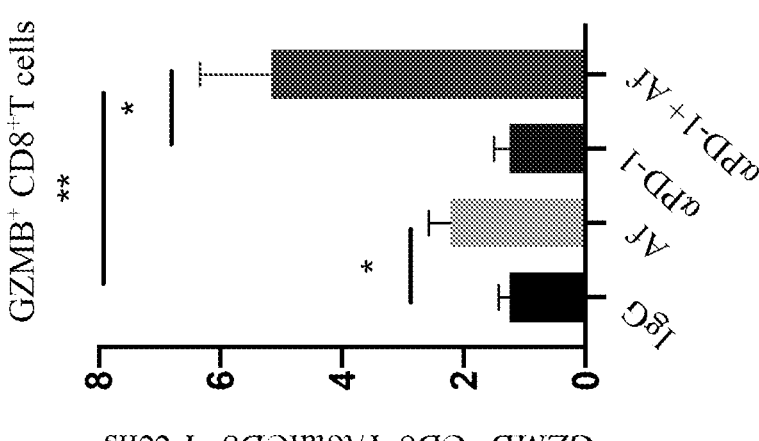

FIG. 10 shows use of flow cytometry for detection of tumor-killing associated immune cells ie, abundancy of granzyme-positive CD8$^+$ T cells, granzyme-positive NK cells and IL-6$^+$ neutrophils, in MC38 mouse model. Results show that compared with the monotherapy group (αPD-1), active Af combination group (αPD-1+Af) significantly increases relative abundance of granzyme-positive CD8$^+$ T cells, granzyme-positive NK cells and IL-6$^+$ neutrophils, demonstrating that active *Alistipes finegoldii* combined with αPD-1 enhances the anti-tumor effect of the immune system.

Embodiment 3 Effect of Active *Alistipes finegoldii* Combined with Different Immune Checkpoint Inhibitors on Prolongation of Overall Survival

I. Experimental Methods

1. Experimental Materials (1) Mice: 6-week-old female C57BL/6J mice (2) Tumor cell lines: murine melanoma cell line (B16-OVA, ATCC), murine colon cancer cell line (MC38, ATCC)

(3) *Alistipes finegoldii* (DSM No.: 17242, Type strain, which 16S rDNA sequence is shown in SEQ ID NO: 1), referred to as Af, commercially purchased from DSMZ German National Culture Collection.

(4) Bacterial culture medium: liquid DSMZ104 culture medium, which formula mainly includes peptone, yeast extract, beef extract and glucose, etc., commercially purchased from DSMZ German National Culture Collection.

(5) Immune checkpoint inhibitors: PD-1 monoclonal antibody (αPD-1), clone number G4C2, the reagent was presented by Shanghai Junshi Biomedical Technology Co., Ltd. CTLA4 monoclonal antibody (αCTLA4), clone number 9D9, was purchased from BioXcell, USA.

(6) Antibiotic combination: metronidazole 100 mg/kg, vancomycin 50 mg/kg, penicillin sodium 100 mg/kg, and neomycin sulfate 100 mg/kg 2. Experimental Grouping The experimental grouping is shown in Table 4.

TABLE 4

| | | | | |
|---|---|---|---|---|
| Experimental grouping | | | | |
| Cell line | Group | Mouse quantity | Dose (each) | Frequency of treatment |
| MC38 | IgG | 6 | 200 μg | every two days |
| | IgG + Af-low | 6 | IgG: 200 μg, Af: 1 × 10⁹ CFU | IgG every two days, Af every one day |
| | IgG + Af -medium | 6 | IgG: 200 μg, Af: 2 × 10⁹ CFU | IgG every two days, Af every one day |
| | IgG + Af-high | 6 | IgG: 200 μg, Af: 4 × 10⁹ CFU | IgG every two days, Af every one day |
| | αPD-1/αCTLA4 | 6 | 200 μg | every two days |
| | αPD-1/αCTLA4 + Af-low | 6 | αPD-1/αCTLA4: 200 μg, Af: 1 × 10⁹ CFU | αPD-1/αCTLA4 every two days, Af every one day |
| | αPD-1/αCTLA4 + Af-medium | 6 | αPD-1/αCTLA4: 200 μg, Af: 2 × 10⁹ CFU | αPD-1/αCTLA4 every two days, Af every one day |
| | αPD-1/αCTLA4 + Af-high | 6 | αPD-1/αCTLA4: 200 μg, Af: 4 × 10⁹ CFU | αPD-1/αCTLA4 every two days, Af every one day |
| B16-OVA | IgG | 6 | 200 μg | every two days |
| | IgG + Af-low | 6 | IgG: 200 μg, Af: 1 × 10⁹ CFU | IgG every two days, Af every one day |
| | IgG + Af -medium | 6 | IgG: 200 μg, Af: 2 × 10⁹ CFU | IgG every two days, Af every one day |
| | IgG + Af-high | 6 | IgG: 200 μg, Af: 4 × 10⁹ CFU | IgG every two days, Af every one day |
| | αPD-1/αCTLA4 | 6 | 200 μg | every two days |
| | αPD-1/αCTLA4 + Af-low | 6 | αPD-1/αCTLA4: 200 μg, Af: 1 × 10⁹ CFU | αPD-1/αCTLA4 every two days, Af every one day |
| | αPD-1/αCTLA4 + Af-medium | 6 | αPD-1/αCTLA4: 200 μg, Af: 2 × 10⁹ CFU | αPD-1/αCTLA4 every two days, Af every one day |
| | αPD-1/αCTLA4 + Af-high | 6 | αPD-1/αCTLA4: 200 μg, Af: 4 × 10⁹ CFU | αPD-1/αCTLA4 every two days, Af every one day |

3. Experimental Steps (1) Active *Alistipes finegoldii* cultivation: *Alistipes finegoldii* was inoculated in DSMZ104 liquid medium, cultured in an anaerobic chamber at 37° C. for 18 hours, and then centrifuged to a concentration of $1 \times 10^{10}$ CFU/ml.

(2) Tumor cells were inoculated subcutaneously, MC38 cells $1 \times 10^6$/mouse, B16-OVA cells $5 \times 10^5$/mouse.

(3) Day 1 to Day 3: the antibiotics combination was administered by gavage to each group of mice to eliminate intestinal inherent flora.

(4) Starting from Day 5, every 3 days, IgG or αPD-1 or αCTLA4 was intraperitoneally injected, 200 μg/mouse.

(5) Starting from Day 5, every 2 days, different doses of active *Alistipes finegoldii* were administered by gavage for treatment, wherein a low dose group (low) was 100 μl/mouse, $1 \times 10^9$ CFU/mouse, and a medium dose group (medium) was 200 μl/mouse, $2 \times 10^9$ CFU/mouse, and a high dose group (high) was 400 μl/mouse, $4 \times 10^9$ CFU/mouse.

(6) Starting from Day 5, every 3 days, a tumor size was masured and a tumor volume was calculated.

$$\text{Tumor volume} = \frac{\text{tumor width}^2 \times \text{tumor length}}{2}$$

(7) A treatment cycle was until the mouse tumor grew to a size (2000 mm³) and then the mouse was euthanized or the mouse did not reach the ethical size of the tumor and died spontaneously.

(8) A death status and time of each mouse was recorded, and a survival curve chart was drawn.

II. Experimental Results

Figure 11:
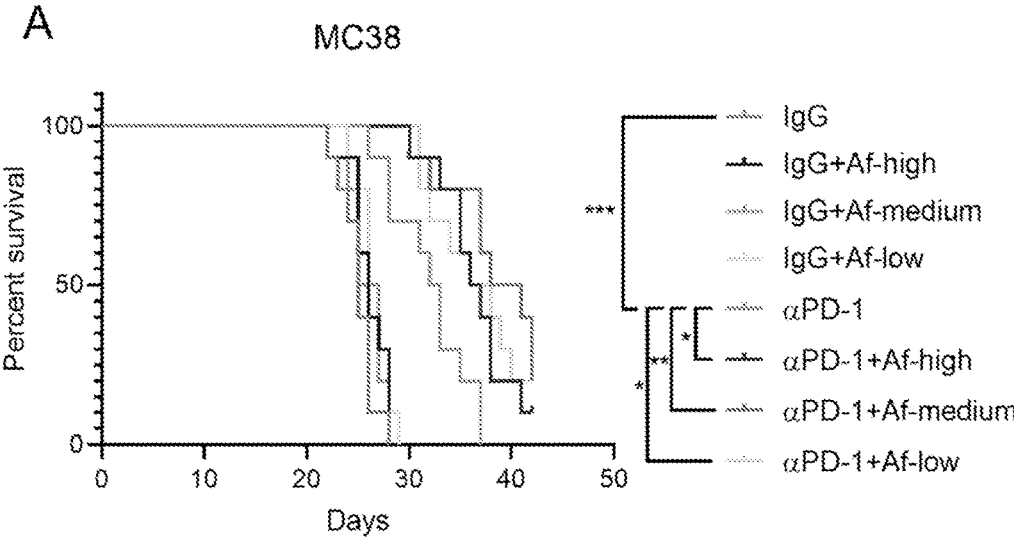
FIG. 11 is a survival curve of mouse models of colon cancer and melanoma administered with different doses of active *Alistipes finegoldii* in Embodiment 3.
Figure 11:
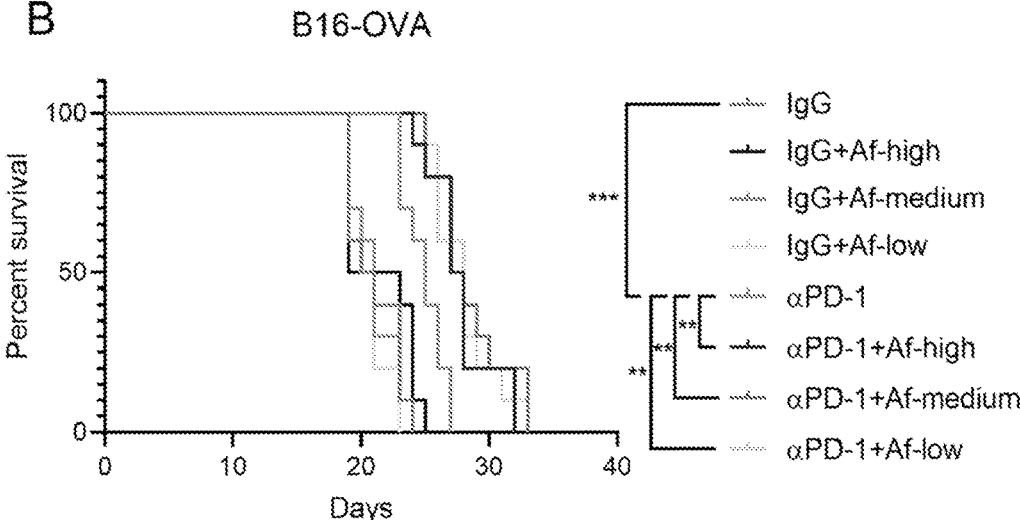
Figure 11:
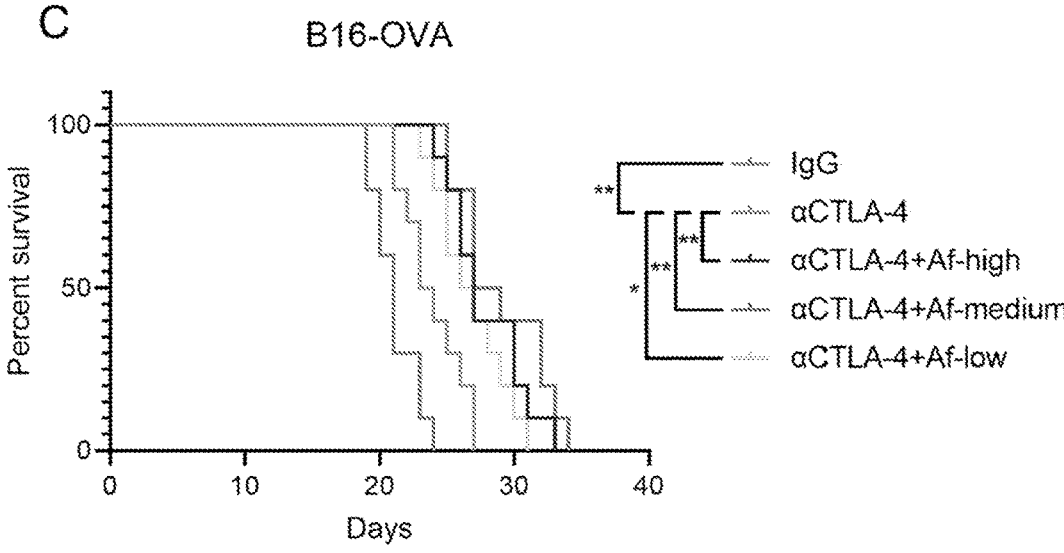

FIG. 11 shows the survival curve of mice. In MC38 colon cancer and B16-OVA melanoma mouse models, compared with the single-agent immune checkpoint inhibitor group (αPD-1), the combination therapy groups (αPD-1+Af) wth high dose (high), medium dose (medium), and a low dose (low) of *Alistipes finegoldii* can all significantly increase survival time of tumor-bearing mice. In the B16-OVA melanoma mouse model, *Alistipes finegoldii* also shows the effect of promoting the efficacy of αCTLA4 immune checkpoint inhibitor: αCTLA4 combined with high, medium and low doses of *Alistipes finegoldii* can all significantly the increase survival time of the tumor-bearing mice. However, in the MC38 colon cancer mouse model, the effect of αCTLA4 immune checkpoint inhibitor is too strong, and a synergistic effect of *Alistipes finegoldii* on αCTLA4 is not observed.

Embodiment 4 Administration of Active and Inactive Whole-Cell *Alistipes finegoldii* Combined with Immune Checkpoint Inhibitors to Treat Colon Cancer

I. Experimental Methods

1. Experimental Materials (1) Mice: 6-week-old female C57BL/6J mice (2) Tumor cell lines: murine colon cancer cell line (MC38, ATCC)

(3) Strain information: *Alistipes finegoldii* (DSM No.: 17242, Type strain, which 16S rDNA sequence is shown in SEQ ID NO: 1), referred to as Af or Af, commercially purchased from German National Culture Collection DSMZ (official website of DSMZ: http://www.dsmz.de).

(4) Medium components: liquid DSMZ104 medium, the formula mainly includes peptone, yeast extract, beef extract and glucose, etc., commercially purchased from DSMZ German National Culture Collection.

(5) Immune checkpoint inhibitors: PD-1 monoclonal antibody (αPD-1), clone number G4C2, the reagent was presented by Shanghai Junshi Biomedical Technology Co., Ltd.

(6) Antibiotic combination: metronidazole 100 mg/kg, vancomycin 50 mg/kg, penicillin sodium 100 mg/kg, neomycin sulfate 100 mg/kg.

2. Experimental Grouping

The experimental grouping is shown in Table 5.

TABLE 5

| Experimental grouping | | | | |
| --- | --- | --- | --- | --- |
| Cell line | Group | Mouse quantity | Dose (each) | Frequency of treatments |
| MC38 colon cancer | Non-treatment group (PBS) | 10 | 200 μl | 3 times |
| | Single-agent therapy group (αPD-1) | 10 | 200 μg | 3 times |
| | Active combination therapy group (αPD-1 + Af) | 7 | αPD-1: 200 μg, active Af: $1 \times 10^9$ CFU | αPD-1 for 3 times, active Af for 5 times |
| | Inactive whole-cell combination therapy group (αPD-1 + Af_heat killed) | 7 | αPD-1: 200 μg, inactive whole-cell Af: $1 \times 10^9$ CFU | αPD-1 for 3 times, inactive whole-cell Af for 5 times |

Note:
Af means *Alistipes finegoldii*

Figure 12:
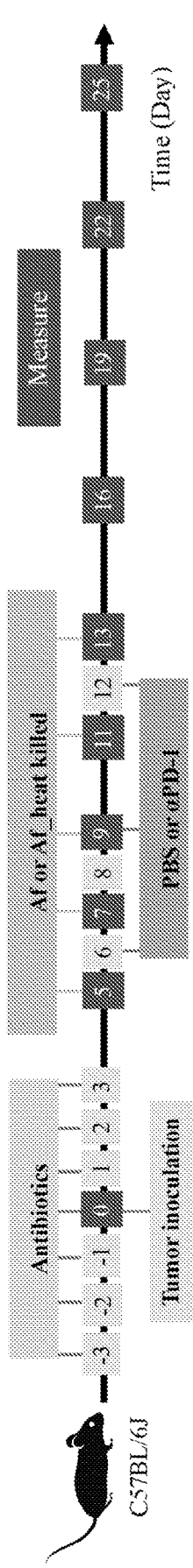
FIG. 12 is a flowchart of administration of active *Alistipes finegoldii* and inactive whole-cell *Alistipes finegoldii* in mouse model of colon cancer in Embodiment 4.

3. Experimental Steps (Process Shown in FIG. 12)

(1) Preparation of active Af (Af): *Alistipes finegoldii* was inoculated in DSMZ104 liquid medium, cultured in an anaerobic chamber at 37° C. for 18 hours, and then centrifuged to a concentration of $1 \times 10^{10}$ CFU/ml. Bacterial cells were washed and concentrated with phosphate buffered saline (PBS) for three times, till the residual medium was washed away.

(2) Preparation of inactive whole-cell Af (heat killed, Af_heat killed): Bacterial cells prepared in (1) were washed and concentrated with phosphate buffered saline (PBS), and heated at a high temperature of 95° C. for 5 minutes.

(3) Subcutaneous inoculation of tumor cells: MC38 cells $1 \times 10^6$/mouse.

(4) Antibiotic treatment: the antibiotics combination was administered by gavage to each group of mice to eliminate intestinal inherent flora, the treatment was for 7 days.

(5) Group treatment: On Day 6, Day 9 and Day 12 respectively, phosphate buffered saline (PBS) or αPD-1 was injected intraperitoneally, 200 μg/mouse. On Day 5, Day 7, Day 9, Day 11, and Day 13 respectively, active Af was administered by gavage or inactive whole-cell Af was orally administered for treatment, 100 μl/mouse, $1 \times 10^9$ CFU/mouse. On Day 0, Day 5, Day 7, Day 9, Day 11, Day 13, Day 16, Day 19, Day 22 and Day 25 respectively, a tumor size was measured and a tumor volume was calculated.

(6) Tumor volume measurement calculation formula:

$$\text{Tumor volume} = \frac{\text{tumor width}^2 \times \text{tumor length}}{2}$$

(7) Intestinal contents of mice were collected at the endpoint (Day 25), and composition of the gut microbiota of mice was analyzed by 16S rRNA gene sequencing, and effects of treatment of colon cancer with active Af and inactive whole-cell Af on intestinal microbiota in mice were compared.

II. Experimental Results

Figure 13:
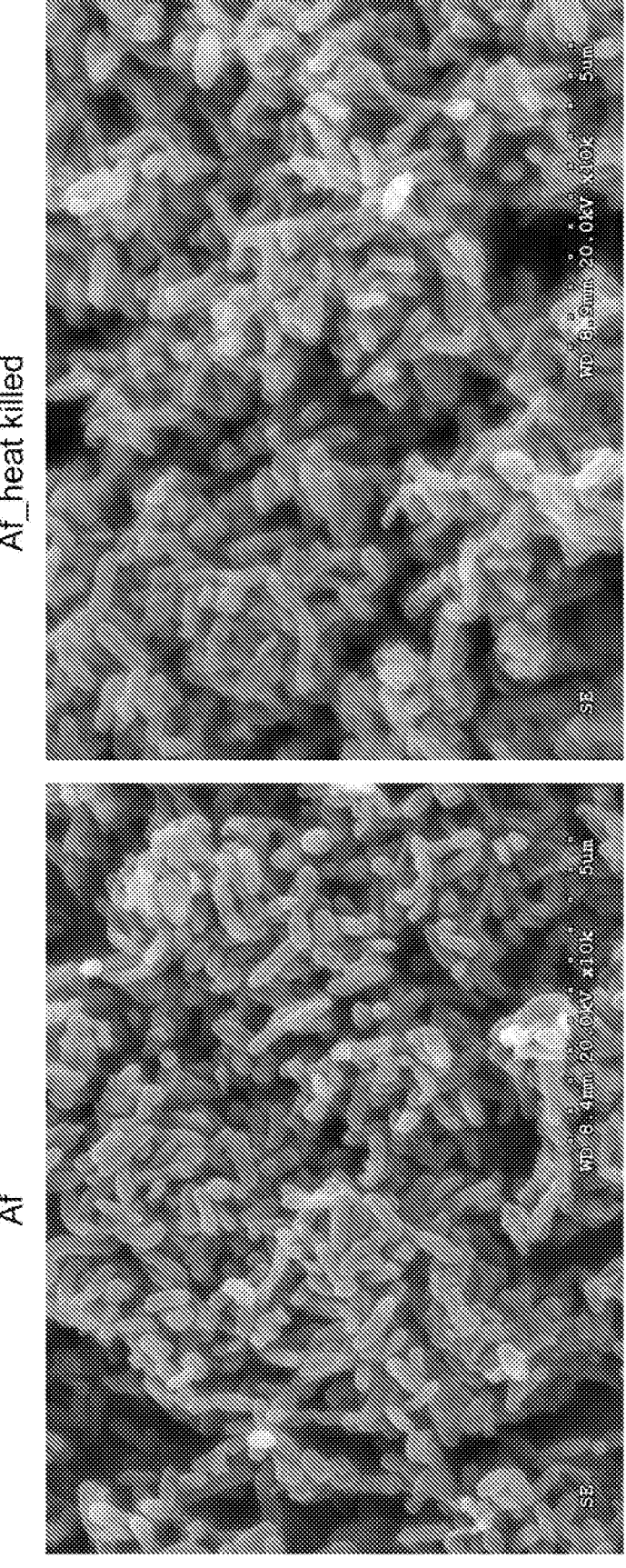
FIG. 13 is a comparison diagram of electron micrographs of active *Alistipes finegoldii* and inactive whole-cell *Alistipes finegoldii* in Embodiment 4.

FIG. 13 is a comparison diagram of electron micrographs of active Af and inactive whole-cell Af. It can be seen that inactive whole-cell treatment can maintain the whole cell integrity of Af cells, indicating that the component of inactive whole-cell Af that exerts an anti-tumor effect is derived from the whole-cell component.

Figure 14:
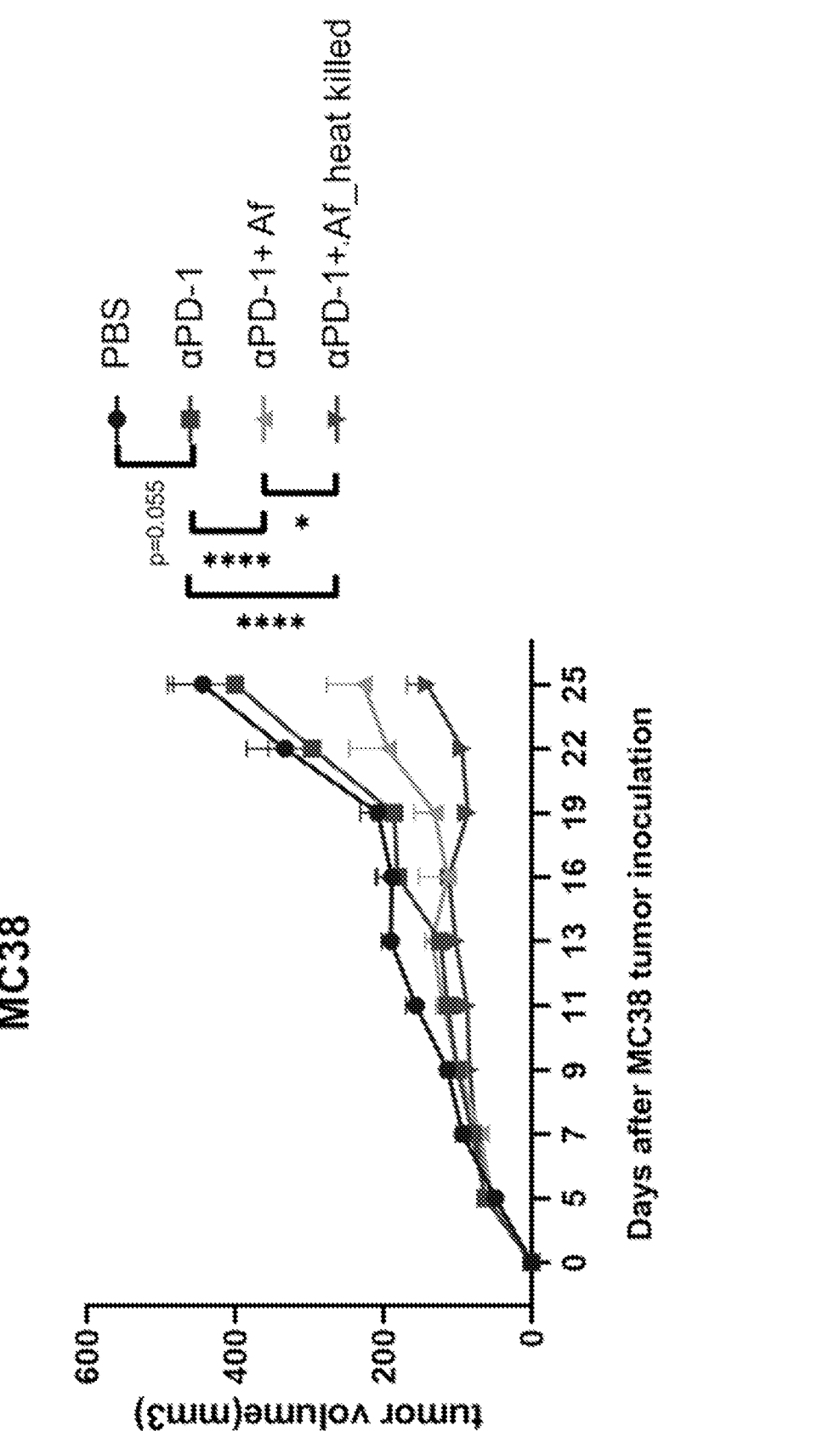
FIG. 14 is a graph showing changes in tumor volume in mouse model of colon cancer administered with active *Alistipes finegoldii* and inactive whole-cell *Alistipes finegoldii* in Embodiment 4.

FIG. 14 is the changes of tumor volume during the treatment of colon cancer with active Af and inactive whole-cell Af. From the comparison of tumor volume changes, in MC38 colon cancer model, compared with the non-treatment group (PBS), the single-agent immune checkpoint inhibitor treatment group (αPD-1) did not show significant (p=0.055) tumor reduction, indicating that colon cancer in this embodiment was resistant to single-agent αPD-1 therapy, while αPD-1 combined with active RX-af01 or inactive whole-cell Af shows significant (*: p<0.001) tumor reduction over the single-agent αPD-1 group after treatment. Comparing therapeutic effects of active Af and inactive whole-cell Af combined with immune checkpoint inhibitor, αPD-1 combined with inactive whole-cell Af shows significant (*: p<0.001) tumor reduction over αPD-1 combined with active Af.

The above results demonstrate that both active Af and inactive whole-cell Af can enhance the anti-tumor effect of immune checkpoint inhibitors. When single-agent αPD-1 is ineffective or resistant, simultaneous administration of αPD-1 combined with active Af or inactive whole-cell Af can reverse the resistance of colon cancer to single-agent αPD-1 treatment, therefore both active Af and inactive whole-cell Af have efficacy to treat, reduce, inhibit or control immune checkpoint inhibitors-refractory tumors, and inactive whole-cell Af may have better anti-tumor effect than active Af.

Figure 15:
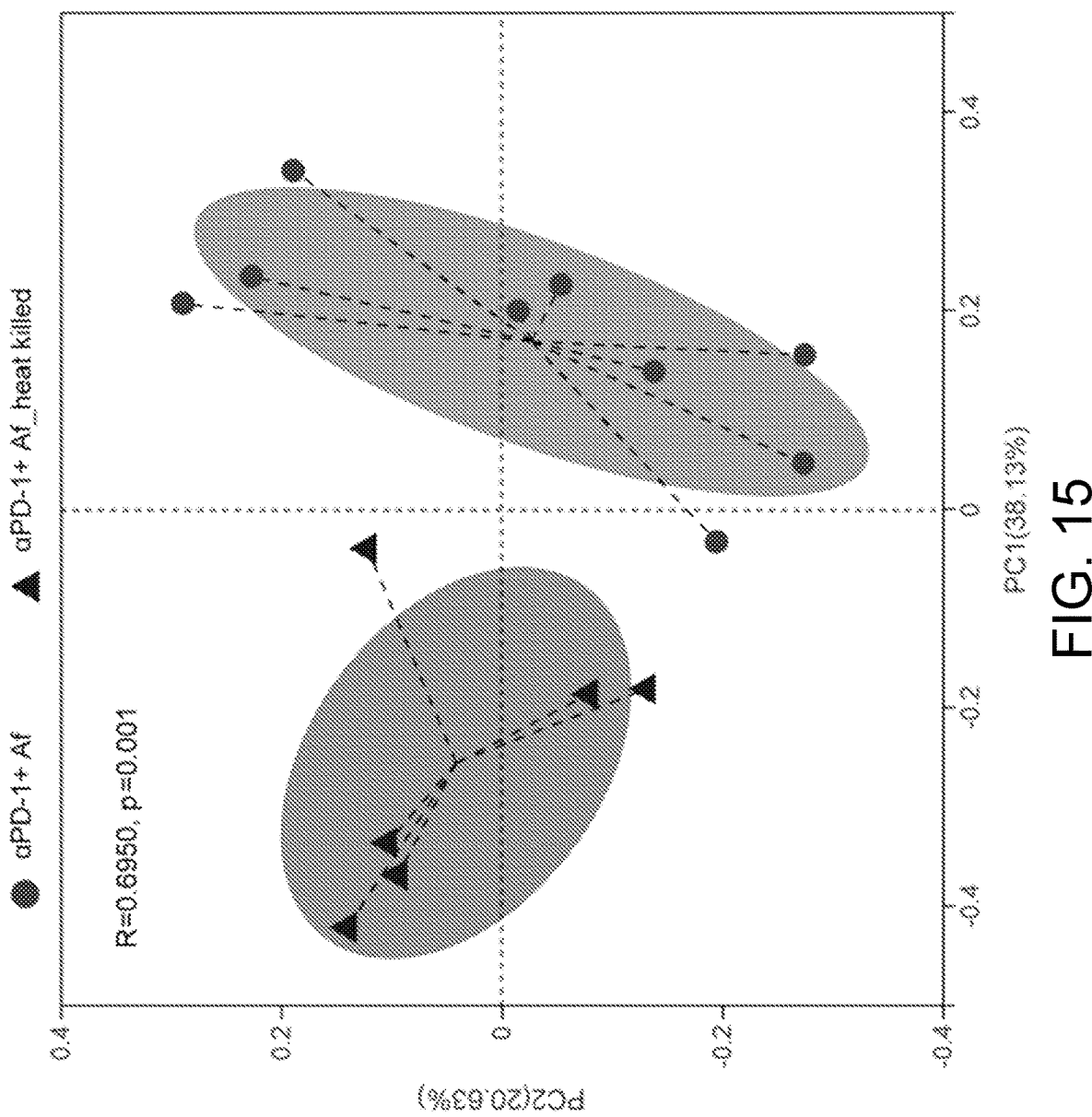
FIG. 15 is β-diversity PCoA analysis of gut microbiome in mouse model of colon cancer administered with active *Alistipes finegoldii* and inactive whole-cell *Alistipes finegoldii* in Embodiment 4.

FIG. 15 is a principal coordinate analysis of β-diversity PCoA (principal co-ordinates analysis) of gut mcirobiome in mouse models of colon cancer treated with active Af and inactive whole-cell Af. The β-diversity of gut mcirobiome refers to composition differences in the overall gut environment bacteria between different intestinal environments; statistical differences between the two groups were measured using Anosim analysis method (Analysis of similarities), Anosim analysis is a nonparametric test method based on permutation test and rank sum test, which is used to test whether the difference between groups is significantly greater than the difference within the group, so as to judge whether the grouping is meaningful. The Anosim method mainly has two numerical results: one is R, its range is [−1, 1], which is used to judge whether there is a difference between different groups, R>0 means that the difference between groups is greater than the difference within the group, R<0 means that the difference between groups is less than the difference within the group, the closer the R value is to 1, the greater the difference between groups; the other is p, which is used to indicate whether there is a significant difference between groups.

Results show that there is a significant and large (R=0.6950, p=0.001) difference in the β-diversity of gut microbiome in mouse models of colon cancer between the treatment of active Af and inactive whole-cell Af. It is demonstrated that treatment of colon cancer with active Af and inactive whole-cell Af can lead to significant and large differences in the composition of the overall gut microbiota, which in turn leads to large differences in the immune status of the gut microbiome. Therefore, in Embodiment 5, the difference in the anti-tumor effects of inactive whole-cell Af and active Af may be related to their different roles of gut microbial remodeling, that is, the reconstruced gut microbiota induced by inactive whole-cell Af combined with αPD-1 correlates with enhanced anti-tumor immune function.

Figure 16:
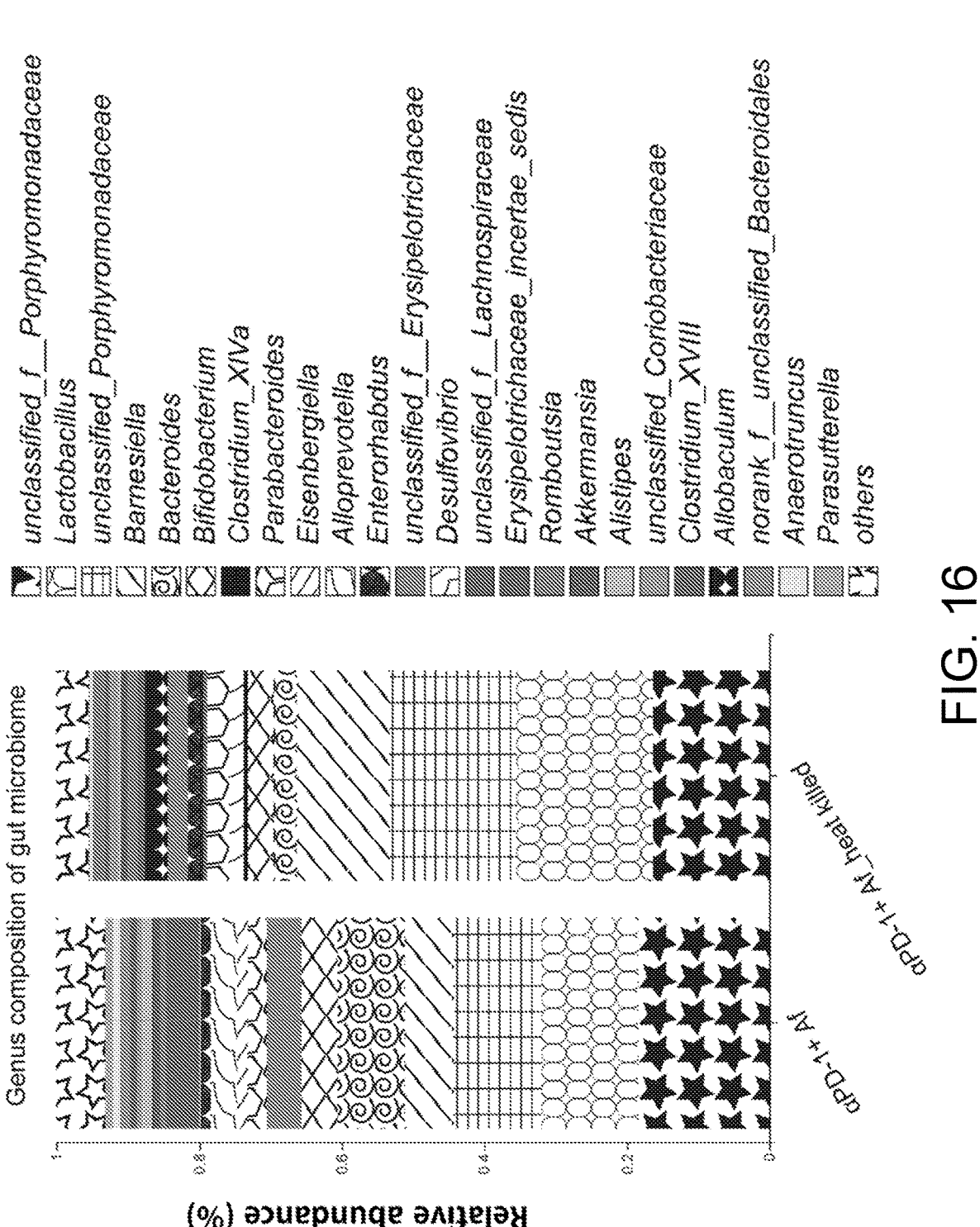
FIG. 16 is a comparison of remodeling effect on gut microbiome by administration of active *Alistipes finegoldii* and inactive whole-cell *Alistipes finegoldii* in mouse model of colon cancer in Embodiment 4.
Figure 17:
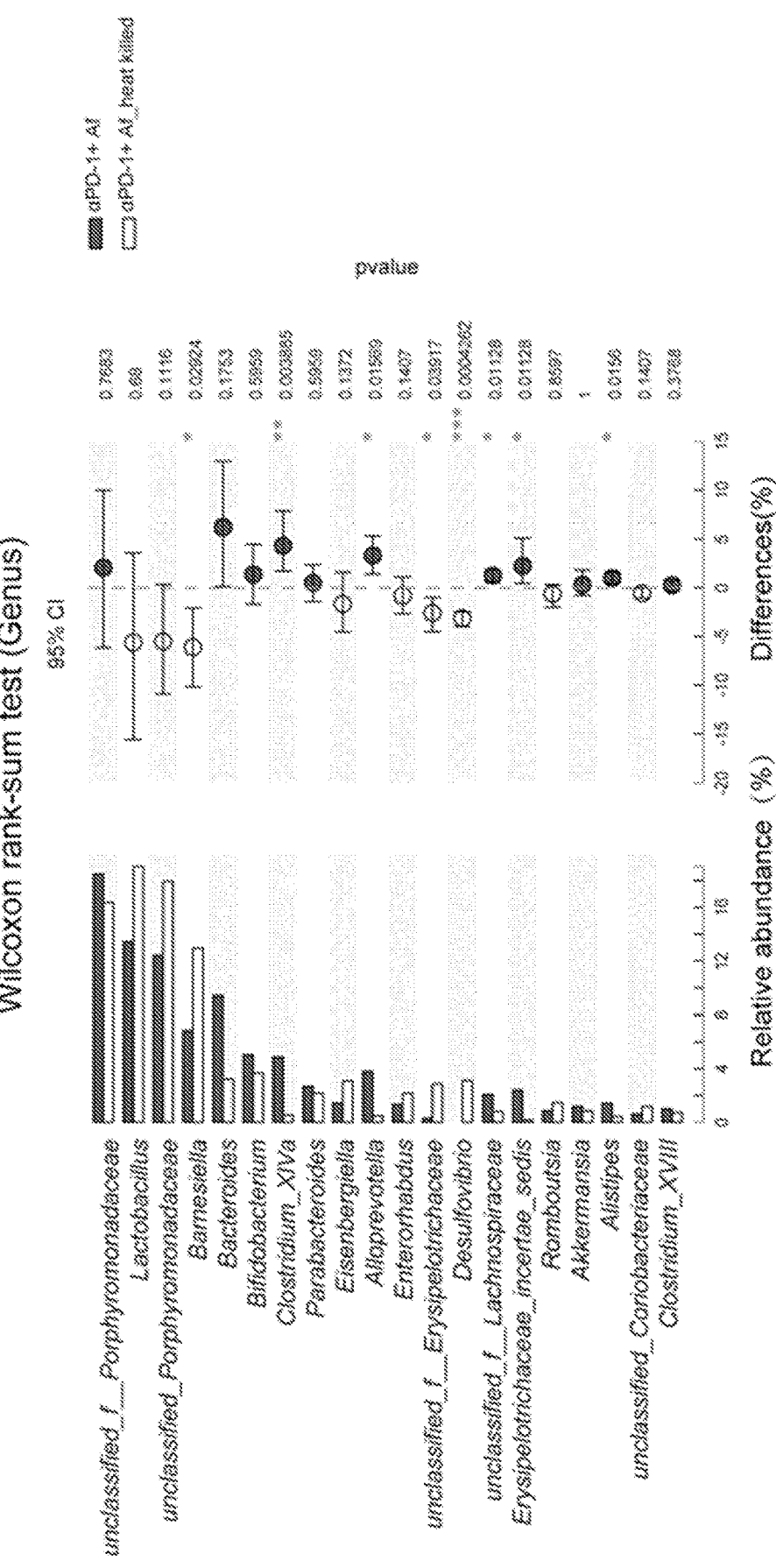
FIG. 17 shows a statistical difference analysis in relative abundance of main bacterial genera (top 20) in mouse model of colon cancer administered with active *Alistipes finegoldii* and inactive whole-cell *Alistipes finegoldii* in Embodiment 4.

FIG. 16 is gut microbiome composition at genus level between the treatment of colon cancer with active Af and inactive whole-cell Af. FIG. 17 shows Wilcoxon rank-sum test statistical difference analysis of the top 20 bacterial genera in the relative abundance of gut microbiome in colon cancer model treated with active Af and inactive whole-cell Af.

Results show that among the top 20 bacterial genera of the gut microbiome in colon cancer model, 8 genera were showed significant statistical differences between the treatments of active Af and inactive whole-cell Af. Among them, the genus *Bacteroides* was showed the largest difference, and the relative abundance of *Bacteroides* in the active Af treatment group was significantly higher than that in the inactive Af treatment group; another prominent difference was for *Desulfovibrio*, which was only present in the inactive whole-cell combination therapy group (αPD-1+Af_heat killed). The relative abundance of *Alistipes*, to which Af belongs, was significantly (p=0.0156) higher in the active combination therapy group than that in the inactive whole-cell combination therapy group. These results demonstrated that treatment of colon cancer with active Af and inactive whole-cell Af lead to significant differences in the gut microbiome composition at the genus level, further resulted in differential intestinal mucosal immune status. Therefore, in Embodiment 4, differences in the anti-tumor effects of active whole-cell Af and inactive whole-cell Af correlates with specific enrichment or weakened of certain bacterial genera in the gut, thereby forming differential intestinal mucosal immune status and stimulating differential anti-tumor immune surveillance.

Embodiment 5 Administration of Active and Inactive Whole-Cell *Alistipes finegoldii* Combined with Immune Checkpoint Inhibitors to Treat Lung Cancer

I. Experimental Methods

1. Experimental Materials (1) Mice: 6-week-old female C57BL/6J mice (2) Tumor cell line: mouse lung cancer cell line (LLC, ATCC)

(3) Af strain information: *Alistipes finegoldii* (DSM No.: 17242, Type strain, which 16S rDNA sequence is shown in SEQ ID NO: 1), commercially available from German National Culture Collection DSMZ (official website of DSMZ: http://www.dsmz.de).

(4) Medium components: liquid DSMZ104 medium, the formula mainly includes peptone, yeast extract, beef extract and glucose, etc., commercially purchased from DSMZ German National Culture Collection.

(5) Immune checkpoint inhibitor: PD-1 monoclonal antibody (αPD-1), clone number G4C2, the reagent was presented by Shanghai Junshi Biomedical Technology Co., Ltd.

(6) Antibiotic combination: metronidazole 100 mg/kg, vancomycin 50 mg/kg, penicillin sodium 100 mg/kg, neomycin sulfate 100 mg/kg

II. Experimental Grouping

The experimental grouping is shown in Table 6.

TABLE 6

| Experimental grouping | | | | |
| --- | --- | --- | --- | --- |
| Cell line | Group | Mouse quantity | Dose (each) | Frequency of treatments |
| LLC lung cancer | Non-treatment group (PBS) | 6 | 150 μl | 4 times |
| | Single-agent therapy group (αPD-1) | 6 | 150 μg | 4 times |

TABLE 6-continued

| | | | | |
|---|---|---|---|---|
| | | Experimental grouping | | |
| Cell line | Group | Mouse quantity | Dose (each) | Frequency of treatments |
| | Active combination therapy group (αPD-1 + Af) | 6 | αPD-1: 200 µg, active Af: 1 × 10⁹ CFU | αPD-1 for 4 times, active Af for 8 times |
| | Inactive whole-cell combination therapy group (αPD-1 + Af_heat killed) | 6 | αPD-1: 150 µg inactive whole-cell Af: 1 × 10⁹ CFU | αPD-1 for 4 times, inactive whole-cell Af for 8 times |

Figure 18:
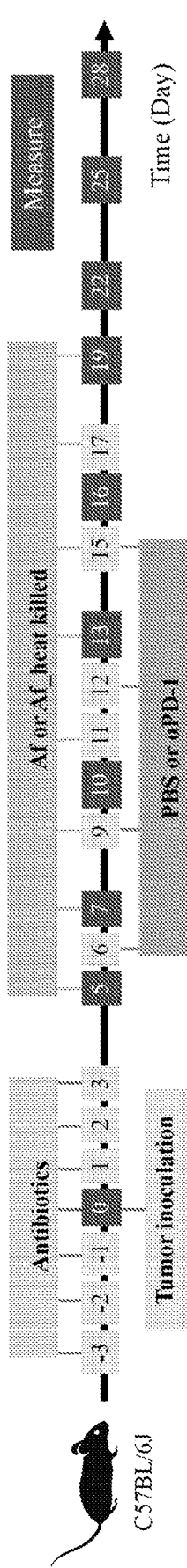
FIG. 18 is a flowchart of administration of active *Alistipes finegoldii* and inactive whole-cell *Alistipes finegoldii* in mouse model of lung cancer in Embodiment 5.

3. Experimental Steps (Process Shown in FIG. 18)

(1) Preparation of active Af: *Alistipes finegoldii* was inoculated in DSMZ104 liquid medium, cultured in an anaerobic chamber at 37° C. for 18 hours, and then centrifuged to a concentration of $1 \times 10^{10}$ CFU/ml. Bacterial cells were washed and concentrated with phosphate buffered saline (PBS) for three times, till the residual medium was washed away.

(2) Preparation of inactive whole-cell Af (heat killed, Af_heat killed): Bacterial cells prepared in (1) were washed and concentrated with phosphate buffered saline (PBS), and heated at a high temperature of 95° C. for 5 minutes.

(3) Subcutaneous inoculation of tumor cells: LLC cell line $1 \times 10^6$/mouse, (4) Antibiotic treatment: the antibiotics combination was administered by gavage to each group of mice to eliminate intestinal inherent flora, the treatment was for 7 days.

(5) Group treatment: On Day 6, Day 9 and Day 12 respectively, phosphate buffered saline (PBS) or αPD-1 was injected intraperitoneally, 150 µg/mouse. On Day 5, Day 7, Day 9, Day 11, Day 13, Day 15, Day 17 and Day 19 respectively, active Af or inactive whole-cell Af was orally administered by gavage for treatment, 100 µl/mouse, $1 \times 10^9$ CFU/mouse. On Day 0, Day 5, Day 7, Day 10, Day 13, Day 16, Day 19, Day 22, Day 25 and Day 28 respectively, a tumor size was measured and a tumor volume was calculated.

(6) Tumor volume measurement calculation formula:

$$\text{Tumor volume} = \frac{\text{tumor width}^2 \times \text{tumor length}}{2}$$

(7) A tumor weight was measured at the endpoint (Day 28), and group statistics were performed.

II. Experimental Results

Figure 19:
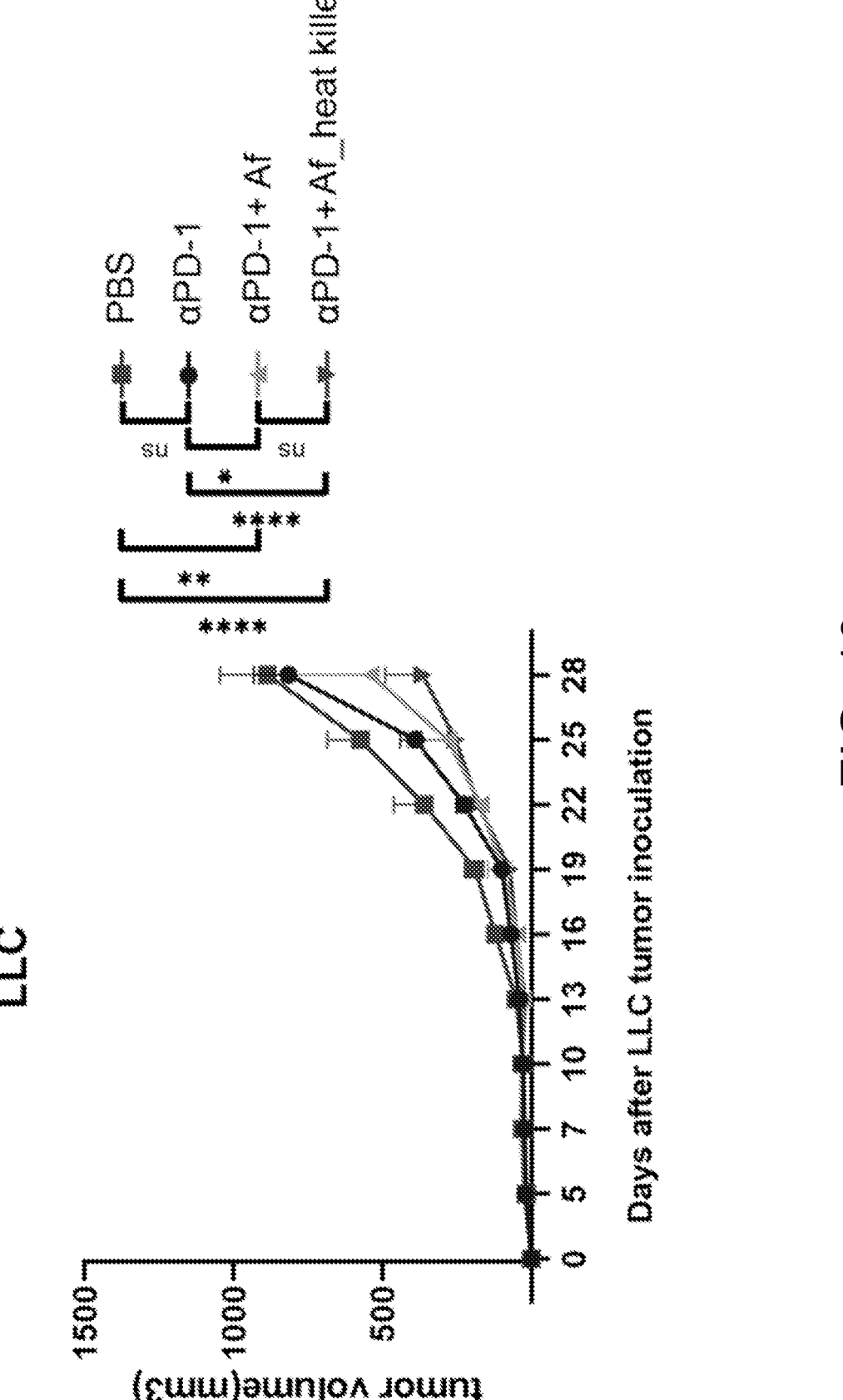
FIG. 19 is a graph showing changes in tumor volume in mouse model of lung cancer administered with active *Alistipes finegoldii* and inactive whole-cell *Alistipes finegoldii* in Embodiment 5.
Figure 20:
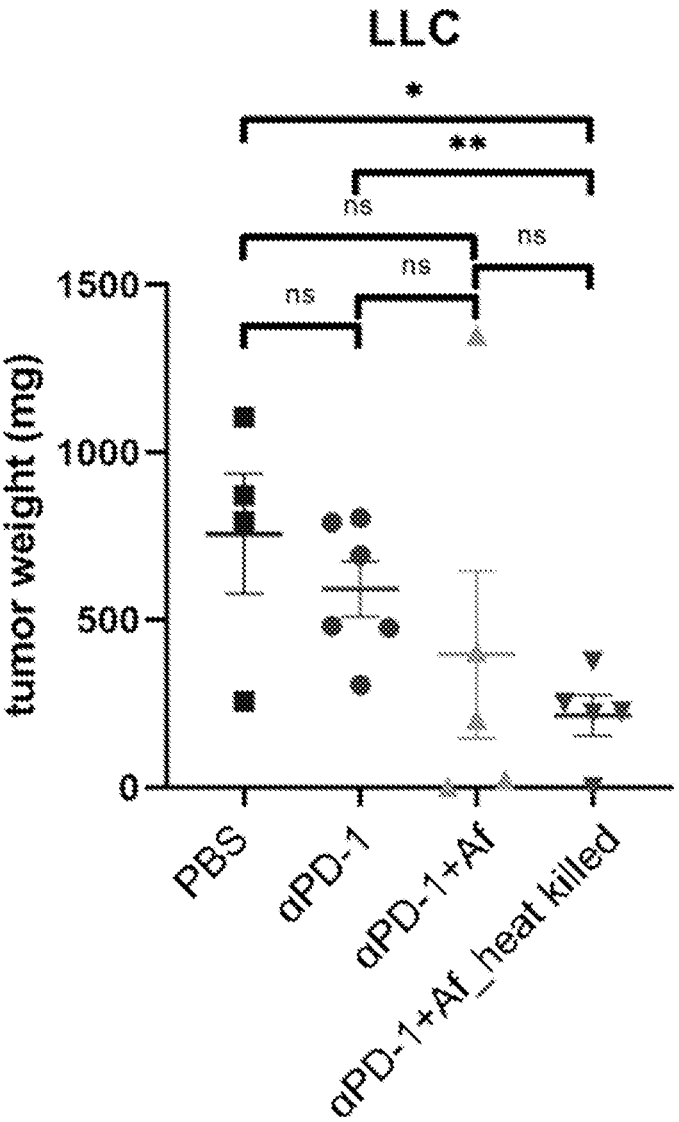
FIG. 20 shows tumor weights at the experimental end point after administration of active *Alistipes finegoldii* and inactive whole-cell *Alistipes finegoldii* in mouse model of lung cancer in Embodiment 5.

FIG. 19 is the changes of tumor volume in lung cancer mouse models administered with active Af and inactive whole-cell Af. The single-agent immune checkpoint inhibitor group (αPD-1) did not show significant (ns: $p > 0.05$) tumor reduction compared with the non-treatment group (PBS), indicating that the single-agent immune checkpoint inhibitor group (αPD-1) in this embodiment was less effective in this LLC mouse lung cancer models and resistant to single-agent αPD-1 therapy; treatment with αPD-1 combined with active Af (αPD-1+Af) or αPD-1 combined with inactive whole-cell Af (αPD-1+Af_heat killed) both showed significant (αPD-1+Af: **p<0.01; αPD-1+Af_heat killed:

****p<0.0001) tumor reduction compared with non-treatment group (PBS); compared with the single-agent immune checkpoint inhibitor group (αPD-1), treatment with αPD-1 combined with active Af (αPD-1+RX-af01) or αPD-1 combined with inactive whole-cell Af (αPD-1+Af_heat killed) groups both showed significantly (αPD-1+Af: *p<0.05; αPD-1+RX-af01_heat killed: **p<0.0001) better tumor treatment effect compared with the single-agent αPD-1; αPD-1 combined with active Af (αPD-1+Af) and αPD-1 combined with inactive whole-cell Af (αPD-1+Af_heat killed) show better tumor treatment effect compared with he single-agent αPD-1; comparing the treatment effects of αPD-1 combined with active Af (αPD-1+RX-af01) or αPD-1 combined with inactive whole-cell Af (αPD-1+Af_heat killed), inactive whole-cell Af shows a trend toward superior efficacy over active Af, but des not reach a statistical significance (ns: $p > 0.05$). FIG. 20 is a tumor weight at the endpoint of treatment in LLC mouse model with active Af and inactive whole-cell Af. The tumor weight at the experimental endpoint shows that compared with non-treatment group (PBS), the single-agent immune checkpoint inhibitor group (αPD-1) does not show significant (ns: $p > 0.05$) tumor reduction. αPD-1 combined with active Af treatment does not show a significantly (ns: $p > 0.05$) superior therapeutic effect over single-agent αPD-1 treatment, while αPD-1 combined with inactive whole-cell Af treatment shows a significantly (p<0.01) superior therapeutic effect over single-agent αPD-1 treatment. Comparing the therapeutic effects of αPD-1 combined with active Af and αPD-1 combined with inactive whole-cell Af, the average weight of inactive whole-cell Af group is lower than that of active Af group. The results demonstrate that both active Af and inactive whole-cell Af can enhance the anti-tumor effect of immune checkpoint inhibitors. When single-agent αPD-1 is ineffective or resistant, concurrent administration of αPD-1 in combination with active Af or inactive whole-cell Af can reverse lung cancer resistance to single-agent αPD-1 therapy, therefore both active Af and inactive whole-cell Af have potency to treat, reduce, inhibit or control immune checkpoint inhibitor-refractory tumors, and the anti-tumor effect of inactive whole-cell Af is superior to that of active Af.

Figure 21:
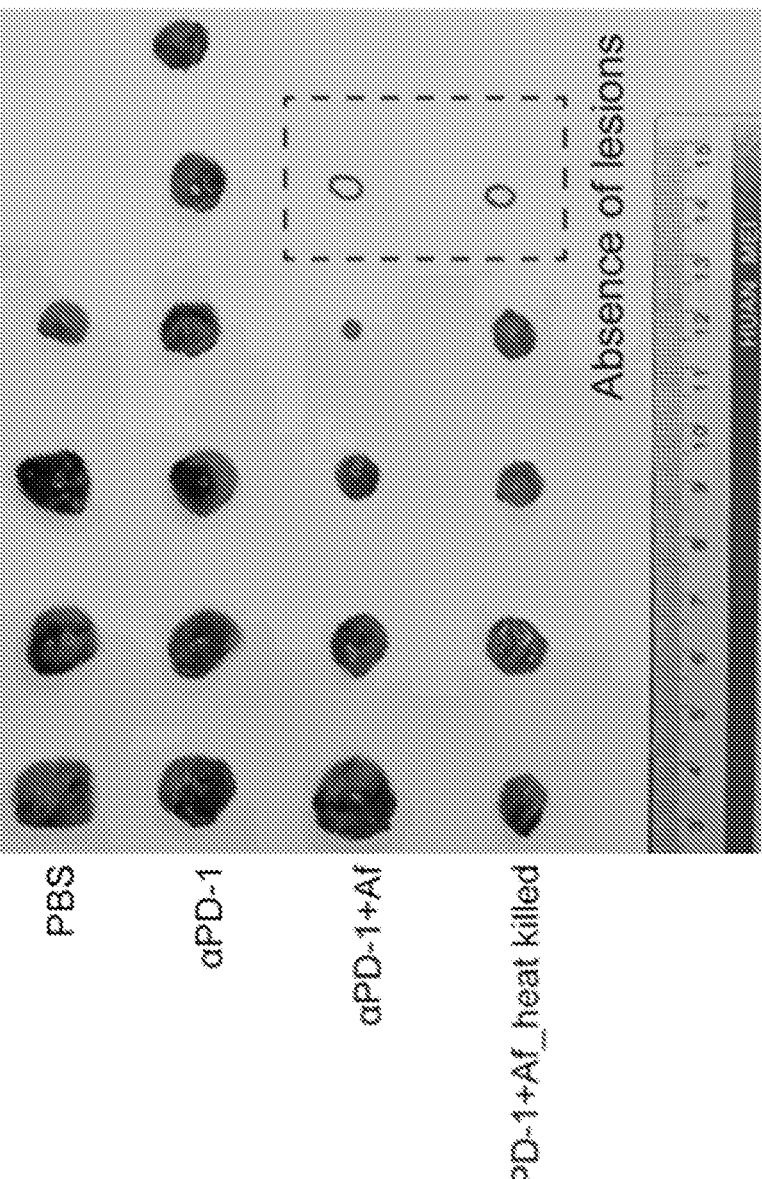
FIG. 21 is a tumor image at the experimental end point after administration of active *Alistipes finegoldii* and inactive whole-cell *Alistipes finegoldii* in mouse model of lung cancer in Embodiment 5.

FIG. 21 is the tumor images at the endpoint of the treatment with active Af and inactive whole-cell Af in LLC mouse model, there is one mouse with complete tumor disappearance in the active combination therapy group (αPD-1+Af) and the inactive whole-cell combination therapy group (αPD-1+Af_heat killed). It is demonstrated that both active Af and inactive whole-cell Af could enhance the anti-tumor effect of immune checkpoint inhibitors.

Embodiment 6 Analysis of the Relative Abundance of *Alistipes Finegoldii* in the Gut and Other Body Sites of Healthy People

I. Implementation Methods and Steps (1) Source of original metagenomic data: metagenomic sequencing data of the public data resources of National Institutes of Health (NIH) Human Microbiome Project (HMP, https://www.hmpdacc.org/) were used.

(2) Bacterial classification and strain-level identification and analysis software: MetaPhlAn2 and StrainPhlAn (https://github.com/biobakery/metaphlan2, https://github-.com/biobakery/metaphlan). Combining MetaPhlAn2 and StrainPhlAn can perform strain-level identification and analysis of metagenomic data. Default settings were used when using these two softwares.

(3) After obtaining the relative abundance of strains (the ratio of a certain strain to the total microbial population) from (2), the abundance of Af in different parts of the body was visualized.

II. Implementation Results

Figure 22:
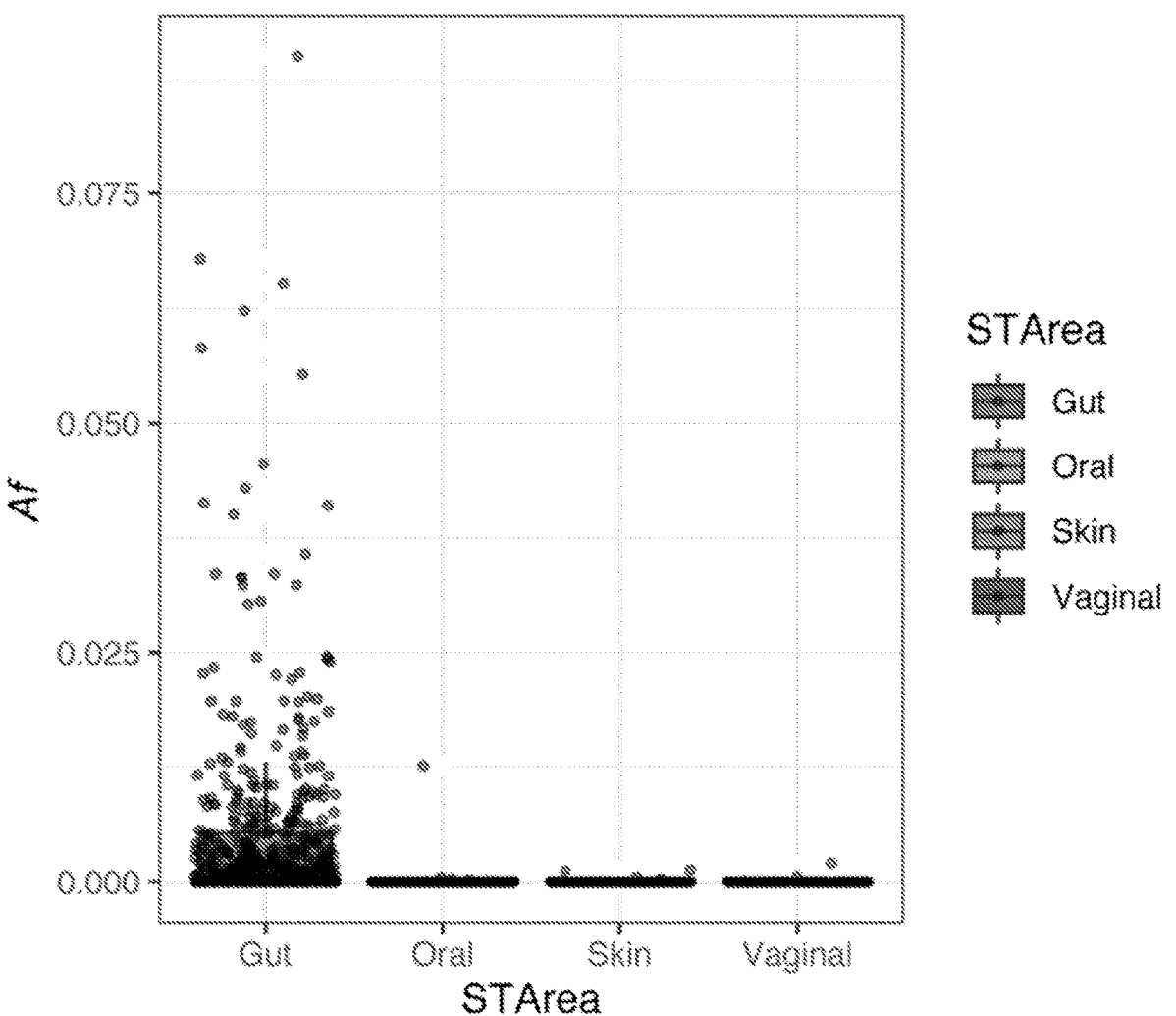
FIG. 22 is relative abundance analysis of *Alistipes finegoldii* in gut and other body sites of healthy people in Embodiment 6.

FIG. 22 shows the relative abundance of Af in the gut and other body sites of healthy people. Analysis of 2335 samples from 4 body sites of healthy people (553 fecal samples, 1259 oral samples, 309 skin samples, 234 vaginal samples) show that Af mainly exists in fecal samples, The positive detection rate in the feces is 73.6% (407/553). In oral, skin and vaginal samples, a detection rate of Af is 1.4% (18/1259), 1.9% (6/309) and 1.7% (4/234), respectively. The relative abundance of Af in 407 Af-positive fecal samples range from 0.00006% to 9.0%. According to the latest estimates of the number of gut microbiota, the total number of bacteria contained in the intestinal tract of a healthy adult male weighing 70 kg is about $3.8*10^{13}$, and the number of Af in the intestinal tract of healthy people in the HMP database is about $10^6$-$10^{13}$ (Sender, Fuchs et al. 2016). Thus, Af interacts with human body as a symbiotic bacterium in intestine. The relative abundance of Af is the dominant species (defined as a bacterium with its relative abundance more than 1% in gut microbiome) in some individuals, which proves the safety of Af with the administration dose of $10^5$-$10^{12}$ in the present invention.

Embodiment 7 Analysis of Relative Abundance of *Alistipes finegoldii* in the Gut of Healthy People and Other Diseased Populations

I. Experimental Methods

Four gut metagenomic datasets from human were analyzed, containing 1,396 human feces samples, involving 9 cohorts with different health status. Metagenomic sequencing technology can reach an accuracy of bacterial species.

Nine different health status: 1) healthy adults; 2) patients with colorectal adenoma; 3) patients with colorectal cancer; 4) patients underwent resection for colorectal cancer; 5) patients with atherosclerosis; 6) patients with non-small cell lung cancer before receiving immune checkpoint inhibitors (ICIs); 7) patients with non-small cell lung cancer after receiving immune checkpoint inhibitors (ICIs); 8) patients with renal cell carcinoma before receiving immune checkpoint inhibitors (ICIs); 9) patients with renal cell carcinoma after receiving immune checkpoint inhibitors (ICIs).

The specific situation of the data sets is shown in Table 7.

TABLE 7

| Public data set of human intestinal metagenome | | |
| --- | --- | --- |
| Datasets | Group | Number |
| Yachida__2019 (n = 347) | Colorectal adenocarcinoma (Adenoma) | 40 |
| | Colorectal cancer (CRC) | 150 |
| | Healthy adults (Healthy) | 127 |
| | Colorectal cancer after surgery (History__surgery) | 30 |
| PRJEB27928 (n = 575) | Colorectal cancer (CRC) | 285 |
| | Healthy adult (Healthy) | 290 |
| PRJEB22863 (n = 219) | Non-small cell carcinoma before treatment (Baseline__NSCLC) | 65 |
| | Renal cell carcinoma before treatment of (Baseline__RCC) | 62 |
| | Non-small cell carcinoma after ICIs treatment of (ICIs__treat__NSCLC) | 53 |
| | Renal cell carcinoma after ICIs treatment of (ICIs__treat__RCC) | 39 |
| VinodK.Gupta__2020 (n = 255) | Atherosclerosis (ACVD) | 152 |
| | Colorectal adenocarcinoma (Adenoma) | 42 |
| | Colorectal cancer (CRC) | 61 |

II. Experimental Results

Figure 23:
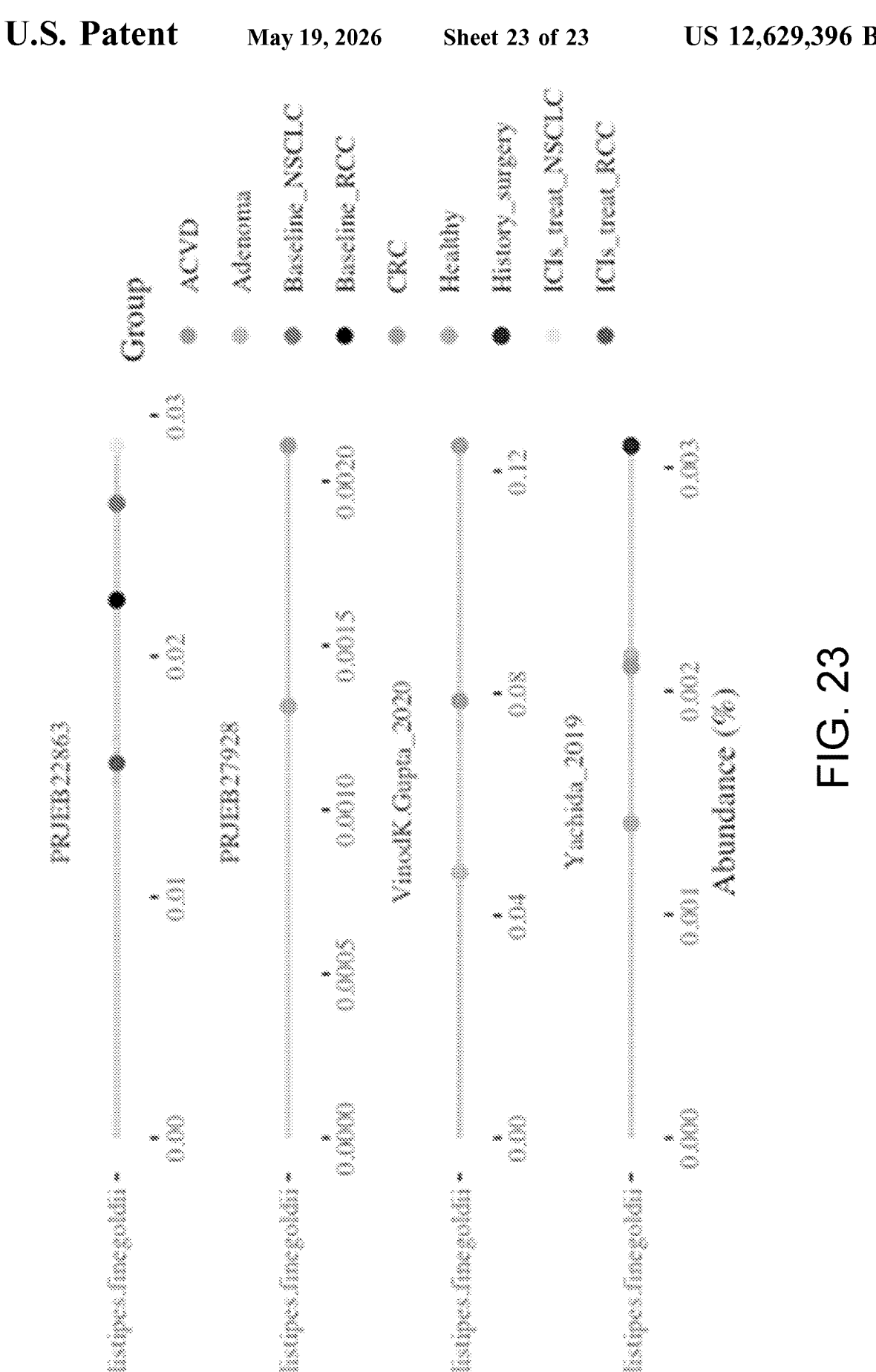
FIG. 23 shows distribution and relative abundance of *Alistipes finegoldii* in gut of different healthy people and other populations in Embodiment 7.

Results in FIG. 23 and Table 8 show that *Alistipes finegoldii* (Af) exists in different populations with a relative abundance of 0.001 to 0.07%, and the relative abundances of Af in different populations have differences, where relative abundance refers to a proportion of a certain bacterial species to all bacterial species in the intestinal tract. According to an estimation that a total number of bacterial species contained in the human intestinal tract is about $10^{14}$ CFU/ml, the number of *Alistipes finegoldii* in the human intestinal tract in these groups is about $10^9$ CFU/ml to $10^{10}$ CFU/ml.

TABLE 8

| Relative abundances of Af in different populations | |
| --- | --- |
| Group | Relative abundance (%) |
| Healthy | 0.001361633 |
| History__surgery | 0.003098462 |

33

TABLE 8-continued

Relative abundances of Af in different populations

| Group | Relative abundance (%) |
|---|---|
| ICIs_treat_RCC | 0.015572821 |
| Baseline_RCC | 0.022339194 |
| Adenoma | 0.024956603 |
| Baseline_NSCLC | 0.026339538 |
| ICIs_treat_NSCLC | 0.028744906 |
| CRC | 0.042939371 |
| ACVD | 0.078639934 |

Finally, it shall be noted that the above embodiments are only used to illustrate the technical solutions of the present invention and not to limit the scope of protection of the present invention. For those of ordinary skill in the art, on the basis of the above description and ideas, other variations or changes can be further made in different forms and it is not necessary and impossible to enumerate all the implementations here. Any modification, equivalent replacement and improvement made within the spirit and principle of the present invention shall be included in the protection scope of the claims of the present invention.

REFERENCES

1. Baruch E N, Y. I., Ben-Betzalel G, Ortenberg R, Lahat A, Katz L, Adler K, Dick-Necula D, Raskin S, Bloch N, Rotin D, Anafi L, Avivi C, Melnichenko J, Steinberg-Silman Y, Mamtani R, Harati H, Asher N, Shapira-Frommer R, Brosh-Nissimov T, Eshet Y, Ben-Simon S, Ziv O, Khan MAW, Amit M, Ajami N J, Barshack I, Schachter J, Wargo J A, Koren O, Markel G, Boursi B. (2020). "Fecal microbiota transplant promotes response in immunotherapy-refractory melanoma patients." Science 5(371(6529)): 8.
2. Derosa, L., B. Routy, A. Desilets, R. Daillere, S. Terrisse, G. Kroemer and L. Zitvogel (2021). "Microbiota-Cen-

34 tered Interventions: The Next Breakthrough in Immuno-Oncology?" Cancer Discov 11(10): 2396-2412.
3. Iida N, D. A., Stewart C A, Smith L, Bouladoux N, Weingarten R A, Molina D A, Salcedo R, Back T, Cramer S, Dai R M, Kiu H, Cardone M, Naik S, Patri A K, Wang E, Marincola F M, Frank K M, Belkaid Y, Trinchieri G, Goldszmid R S (2013). "Commensal bacteria control cancer response to therapy by modulating the tumor microenvironment." Science 22(342(6161)): 4.
4. Mager L F, B. R., Pett N, Cooke N C A, Brown K, Ramay H, Paik S, Stagg J, Groves R A, Gallo M, Lewis I A, Geuking M B, McCoy K D. (2020). "Microbiome-derived inosine modulates response to checkpoint inhibitor immunotherapy." Sciense 18(369(6510)): 10.
5. Parker, B. J., P. A. Wearsch, A. C. M. Veloo and A. Rodriguez-Palacios (2020). "The Genus Alistipes: Gut Bacteria With Emerging Implications to Inflammation, Cancer, and Mental Health." Frontiers in Immunology 11.
6. Routy B, L. C. E., Derosa L, Duong C P M, Alou M T, Daillère R, Fluckiger A, Messaoudene M, Rauber C, Roberti M P, Fidelle M, Flament C, Poirier-Colame V, Opolon P, Klein C, Iribarren K, Mondragón L, Jacquelot N, Qu B, Ferrere G, Clémenson C, Mezquita L, Masip J R, Naltet C, Brosseau S, Kaderbhai C, Richard C, Rizvi H, Levenez F, Galleron N, Quinquis B, Pons N, Ryffel B, Minard-Colin V, Gonin P, Soria J C, Deutsch E, Loriot Y, Ghiringhelli F, Zalcman G, Goldwasser F, Escudier B, Hellmann M D, Eggermont A, Raoult D, Albiges L, Kroemer G, Zitvogel L (2018). "Gut microbiome influences efficacy of PD-1-based immunotherapy against epithelial tumors." Sciense 5(359(6371)): 7.
7. Sender, R., S. Fuchs and R. Milo (2016). "Revised Estimates for the Number of Human and Bacteria Cells in the Body." PLoS Biol 14(8): e1002533.
8. Zipkin, M. (2021). "Fecal microbiota potentiate checkpoint inhibitors, unleash microbiome startups." Nat Biotechnol 39(5): 529-532.

What is claimed is:

1. A product for tumor treatment, the product comprising one or more of immune checkpoint inhibitors, and a bacterium;

the immune checkpoint inhibitor is an inhibitor that acts on PD-1/PD-L1 signaling pathway and/or PD-1/PD-L2 signaling pathway, wherein the PD-1 refers to programmed cell death protein 1, the PD-L1 refers to B7-H1 or CD274, and the PD-L2 refers to B7-DC or CD273, or an inhibitor that acts on CTLA-4/B7-1 signaling pathway and/or CTLA-4/B7-2 signaling pathway, wherein the CTLA-4 refers to cytotoxic T lymphocyte protein 4, the B7-1 refers to CD80 and the B7-2 refers to CD86;

the bacterium is *Alistipes finegoldii;* the bacterium is active bacteria or inactive whole-cell bacteria.

2. The product according to claim 1, wherein a 16S rDNA sequence of the *Alistipes finegoldii* has at least 99.5% consistency with a 16S rDNA sequence of a *Alistipes finegoldii* strain DSM17242.

3. The product according to claim 1, wherein the *Alistipes finegoldii* is one of or a combination of a plurality of *Alistipes finegoldii* strains.

4. The product according to claim 3, wherein the *Alistipes finegoldii* strain is one of or a combination of a plurality of the following strains:

*Alistipes finegoldii* strain deposited at German collection of microorganisms and cell cultures DSMZ, under accession number DSM 17242;

*Alistipes finegoldii* strain deposited at Japan JCM Culture Collection, under accession number JCM 16770;

*Alistipes finegoldii* strain deposited at Korean KCTC Culture Collection, under accession number KCTC 15236;

*Alistipes finegoldii* strain deposited at Finland Helsinki Anaerobe Reference Laboratory, under accession number AHN 2437;

*Alistipes finegoldii* strain deposited at Sweden CCUG Culture Collection, under accession number CCUG 46020;

*Alistipes finegoldii* strain deposited at French CIP Culture Collection, under accession number CIP 107999; and

*Alistipes finegoldii* strain deposited at Guangdong Micro-organism Culture Collection, under accession number GDMCC 1.2324.

5. The product according to claim 1, wherein the active bacteria are intact bacteria and/or intact viable bacteria.

6. The product according to claim 1, wherein the inactive whole-cell bacteria are obtained by first culturing and expanding the bacteria and then inactivating the bacteria by an inactivation method.

7. The product according to claim 6, wherein the inactivation method is selected from any one or more of high temperature inactivation, high pressure inactivation, ultra-violet inactivation, radiation inactivation and inactivation of at least one chemical agent, and the at least one chemical agent is selected from any one or more of formaldehyde, acetone, and phenol.

8. The product according to claim 1, wherein the inhibitor that acts on PD-1/PD-L1 signaling pathway and/or PD-1/PD-L2 signaling pathway is selected from at least one of nivolumab, pembrolizumab, azetolizumab, atezolizumab, camrelizumab, tislelizumab, durvalumab, spartalizumab, avelumab, sintilimab, toripalimab, cemiplimab, MGA012, MGD013, MGD019 (PD-1/CTLA-4 double antibody), MEDI0680, PDR001, and FAZ053.

9. The product according to claim 1, wherein the immune checkpoint inhibitor is selected from at least one of ipilim-umab, tremelimumab, and MGD019.

10. A method for treating a tumor with a bacterium, wherein the immune checkpoint inhibitor and the bacterium in the product of claim 1 are administered simultaneously, separately or sequentially.

11. The method according to claim 10, wherein treating the tumor comprises one of or a combination of a plurality of shrinking or stabilizing the tumor, prolonging a total survival time, prolonging a progression-free survival, and improving a life quality.

12. The method according to claim 10, wherein the tumor is an adenoma, a malignant tumor, or an adenocarcinoma, wherein the tumor is one or more of adrenocortical carci-noma, bladder urothelial carcinoma, breast cancer, pancre-atic cancer, cervical cancer, cholangiocarcinoma, colon can-cer, colorectal cancer, diffuse large B-cell lymphoma, glioblastoma multiforme, glioma, head and neck cancer, chromophobe renal cell carcinoma, mixed renal cancer, kidney cancer, leukemia, lymphadenoma, brain cancer, liver cancer, lung adenocarcinoma, lung squamous cell carci-noma, mesothelioma, ovarian cancer, pancreatic cancer, pheochromocytoma, paraganglioma, prostate cancer, rectal adenocarcinoma, sarcoma, skin melanoma, stomach cancer, esophageal cancer, testicular cancer, thyroid cancer, thymic cancer, endometrial cancer, uterine sarcoma, uveal mela-noma, and soft tissue sarcoma.

13. The method according to claim 10, wherein the tumor is a malignant tumor, a metastatic tumor, or a non-metastatic tumor.

14. The method according to claim 10, wherein the bacterium is administered by oral administration.

* * * * *